(12) United States Patent
Moloney et al.

(10) Patent No.: US 8,273,905 B2
(45) Date of Patent: Sep. 25, 2012

(54) AMINOALKYL-AMIDOMETHYL-SUBSTITUTED 2-(4-SULPHONYLAMINO)-3-HYDROXY-3,4-DIHYDRO-2H-CHROMAN-6-YL DERIVATIVES

(75) Inventors: Brian Moloney, Didcot (GB); Lester Marrison, Didcot (GB); Dieter Ziegler, Hemmingen (DE); Michael Mlinaric, Hannover (DE); Christiane Boecker, Hannover (DE); Reinhard Brueckner, Hannover (DE); Michael Weske, Burgdorf (DE); Klaus Witte, Hannover (DE); Yvan Fischer, Barsinghausen (DE)

(73) Assignee: Abbott Products GmbH, Hannover (DE)

( * ) Notice: Subject to any disclaimer, the term of this patent is extended or adjusted under 35 U.S.C. 154(b) by 684 days.

(21) Appl. No.: 12/394,662

(22) Filed: Feb. 27, 2009

(65) Prior Publication Data

US 2009/0203686 A1 Aug. 13, 2009

Related U.S. Application Data

(62) Division of application No. 11/400,283, filed on Apr. 10, 2006.

(60) Provisional application No. 60/670,252, filed on Apr. 12, 2005.

(30) Foreign Application Priority Data

Apr. 12, 2005 (EP) .................................... 05102868

(51) Int. Cl.
C07D 311/00 (2006.01)
C07D 411/00 (2006.01)
C07D 405/00 (2006.01)

(52) U.S. Cl. ........ 549/400; 549/401; 544/111; 544/151; 544/376; 546/196; 548/525

(58) Field of Classification Search .................. 549/400, 549/401; 544/111, 151, 376; 546/196; 548/525
See application file for complete search history.

(56) References Cited

U.S. PATENT DOCUMENTS

| 4,882,353 | A | 11/1989 | Niewohner et al. |
| 5,082,858 | A | 1/1992 | Garcia et al. |
| 5,104,890 | A | 4/1992 | Shiokawa et al. |
| 5,151,442 | A | 9/1992 | Garcia et al. |
| 5,637,739 | A | 6/1997 | Jacobsen et al. |
| 5,663,393 | A | 9/1997 | Jacobsen et al. |
| 6,150,356 | A | 11/2000 | Lloyd et al. |
| 6,177,449 | B1 | 1/2001 | Brendel et al. |
| 7,368,582 | B2 * | 5/2008 | Sykes et al. ................... 549/399 |
| 2004/0152763 | A1 | 8/2004 | Ohara et al. |
| 2005/0148659 | A1 | 7/2005 | Sykes et al. |

FOREIGN PATENT DOCUMENTS

| EP | 0 315 009 A2 | 5/1989 |
| EP | 0 370 901 A1 | 5/1990 |
| EP | 0 389 861 A1 | 10/1990 |
| EP | 0 906 911 A1 | 4/1999 |
| WO | WO 91/14694 A1 | 10/1991 |
| WO | WO 00/12077 A1 | 3/2000 |
| WO | WO 00/58300 A1 | 10/2000 |
| WO | WO 02/42285 A1 | 5/2002 |
| WO | WO 03/000675 A1 | 1/2003 |
| WO | WO 2005/037780 A2 | 4/2005 |

OTHER PUBLICATIONS

W. Hu et al., "Depolarization-Induced $^{86}Rb^+$ Efflux in CHO Cells Expressing a Recombinant Potassium Channel", Journal of Pharmacological and Toxicological Methods 34, 1995, (pp. 1-7).

C. Beeton et al., "Selective Blocking of Voltage-Gated $K^+$ Channels Improves Experimental Autoimmune Encephalomyelitis and Inhibits T Cell Activation[1]", The Journal of Immunology 166, 2001, (pp. 936-944).

J. Xu et al., "The voltage-gated potassium channel Kv1.3 regulates energy homeostasis and body weight", Human Molecular Genetics 2003, vol. 12 No. 5, (pp. 551-559).

J. Plasek, K. Sigler, "Slow fluorescent indicators of membrane potential: a survey of different approaches to probe response analysis", Journal of Photochemistry and Photobiology 33, 1996, (pp. 101-124).

M. Garcia-Calvo et al., "Purification, Characterization, and Biosynthesis of Margatoxin, a Component of *Centruroides margaritatus* Venom That Selectively Inhibits Voltage-dependent Potassium Channels" Journal of Biological Chemistry, vol. 268, No. 25, 1993 (pp. 18866-18874).

* cited by examiner

*Primary Examiner* — Andrew D Kosar
*Assistant Examiner* — Raymond Covington
(74) *Attorney, Agent, or Firm* — Crowell & Moring LLP

(57) ABSTRACT

Compounds corresponding to formula I,

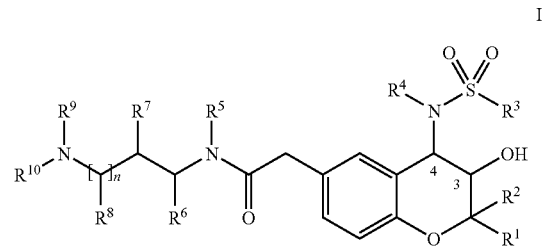

wherein $R^1$, $R^2$, $R^3$, $R^4$, $R^5$, $R^6$, $R^7$, $R^8$, $R^9$, $R^{10}$ and n have the meanings given in the description, and also a process for the preparation of these compounds and intermediate products of this process. Furthermore, pharmaceutical compositions comprising the compounds of Formula I and related methods of treatment.

13 Claims, No Drawings

AMINOALKYL-AMIDOMETHYL-SUBSTITUTED 2-(4-SULPHONYLAMINO)-3-HYDROXY-3,4-DIHYDRO-2H-CHROMAN-6-YL DERIVATIVES

CROSS-REFERENCE TO RELATED APPLICATIONS

This application is a division of our co-pending application Ser. No. 11/400,283, filed Apr. 10, 2006, which in turn claimed benefit under 35 U.S.C. §119(e) from U.S. provisional patent application Ser. No. 60/670,252, filed Apr. 12, 2005, and also claims benefit from European patent application Serial No. EP 05102868.6, filed Apr. 12, 2005, the entire disclosures of which are hereby incorporated in their entirety.

FIELD OF THE INVENTION

The present invention relates to novel aminoalkyl-amidomethyl-substituted 2-(4-sulphonylamino)-3-hydroxy-3,4-dihydro-2H-chromen-6-yl derivatives with a potassium channel-blocking effect, in particular with an effect influencing the cardiovascular system, and also to pharmaceutical formulations containing these compounds and related methods of treatment. Furthermore, the invention relates to a process for the preparation of the novel compounds and intermediate products of this process.

BACKGROUND

Indanes, benzopyrans and analogues of such compounds which have potassium channel-blocking effects, and in particular effects beneficially influencing the cardiovascular system, are already known from specification WO 00/12077 A1 (equivalent to U.S. Pat. No. 6,150,356).

Document WO 00/58300 discloses chroman derivatives which are suitable as pharmaceutical formulations, in particular antiarhythmically effective pharmaceutical formulations.

Published international patent application WO 2005/037780 (equivalent to US 2005/0148659) refers to novel amidomethyl-substituted 2-(4-sulphonylamino)-3-hydroxy-3,4-dihydro-2H-chromen-6-yl derivatives with a potassium channel-blocking effect, in particular with an effect influencing the cardiovascular system, and also to pharmaceutical formulations containing these compounds.

SUMMARY OF THE INVENTION

It was an object of certain embodiments of the present invention to make available novel active substances for the treatment of in particular cardiovascular diseases, preferably cardiac arrhythmias, which are distinguished by high effectiveness with good compatibility and in the case of antiarrhythmic action also by a marked atrial-selective action profile.

It has now surprisingly been found that a group according to the invention of novel aminoalkyl-amidomethyl-substituted 2-(4-sulphonylamino)-3-hydroxy-3,4-dihydro-2H-chromen-6-yl derivatives possess potassium channel-blocking properties and are suitable for the treatment of cardiovascular diseases, preferably for the treatment of cardiac arrhythmias.

The compounds according to the invention are distinguished by high effectiveness with good compatibility and in the case of anti-arrhythmic action also by a marked atrial-selective action profile. Furthermore, the compounds according to the invention are characterized by comparatively good bioavailability. In addition, the compounds according to the invention have properties which lead one to expect an additional effect influencing the immune system.

The subject of the invention is novel aminoalkyl-amidomethyl-substituted 2-(4-sulphonylamino)-3-hydroxy-3,4-dihydro-2H-chromen-6-yl derivatives of the general Formula I,

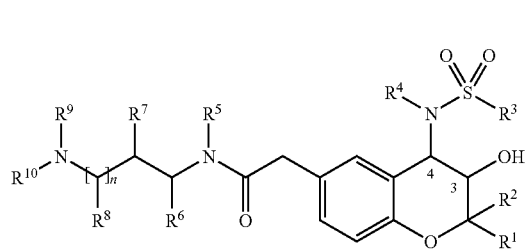

wherein
$R^1$ is $C_{1-4}$-alkyl;
$R^2$ is $C_{1-4}$-alkyl;
$R^3$ is phenyl which is optionally substituted 1 to 3 times by any of halogen, $C_{1-6}$-alkyl or $C_{1-4}$-alkoxy;
$R^4$ is hydrogen; $C_{1-6}$-alkyl or $C_{3-7}$-cycloalkyl-$C_{1-4}$-alkyl,
$R^5$ is hydrogen; and
$R^6$ is hydrogen; and
$R^7$ is hydrogen; and
$R^8$ is hydrogen; and
$R^9$ is $C_{1-4}$-alkyl; and
$R^{10}$ is $C_{1-6}$-alkyl; phenyl-$C_{0-4}$-alkyl or pyridinyl-$C_{0-4}$-alkyl; with the proviso that $R^{10}$ is not phenyl when $R^5$ and $R^9$ together form $C_2$-alkylene; or
$R^5$ and $R^9$ together form $C_{1-3}$-alkylene; or
$R^6$ and $R^9$ together form $C_{1-3}$-alkylene; or
$R^7$ and $R^9$ together form $C_{2-4}$-alkylene or $C_{1-3}$-alkylenoxy; or
$R^8$ and $R^9$ together form $C_{3-5}$-alkylene; or
$R^9$ and $R^{10}$ together form $C_{4-6}$-alkylene; and
n is 0 or 1,
or any physiologically compatible salts and/or solvates thereof.

Furthermore, a subject of certain embodiments of the invention is pharmaceutical compositions containing the compounds of Formula I. Furthermore, a subject of certain embodiments of the invention is a process for the preparation of the compounds of Formula I and intermediate products of this process.

Where, in the compounds of Formula I or in other compounds described within the context of the present invention, substituents are or contain $C_{1-4}$-alkyl or $C_{1-6}$-alkyl, these may each be straight-chain or branched.

$R^1$ and $R^2$ preferably each have the meaning methyl.

$R^3$ preferably has the meaning phenyl which is optionally substituted 1 to 2 times by halogen, $C_{1-4}$-alkyl, or $C_{1-4}$-alkoxy. In particular, $R^3$ has the meaning of phenyl substituted once by $C_{1-4}$-alkyl. Where $R^3$ is halogen-substituted phenyl, fluorine, chlorine or bromine and iodine are considered as halogen. As a particularly preferred meaning, $R^3$ stands for 4-ethylphenyl.

$R^4$ is preferably hydrogen; $C_{1-6}$-alkyl or cyclopropyl-$C_{1-4}$-alkyl, in particular cyclopropylmethyl. Where $R^4$ stands for $C_{1-6}$-alkyl, this is in particular branched and preferably represents neopentyl, 2,2-dimethylbutyl, 2-ethylbutyl, 3-methylbutyl or 2-methylpropyl.

Preferably, $R^5$ and $R^9$ together form $C_{1-3}$-alkylene.

$R^{10}$ is preferably $C_{1-4}$-alkyl; benzyl or phenyl. More preferably, $R^{10}$ is phenyl-$C_{1-4}$-alkyl or pyridinyl-$C_{1-4}$-alkyl, e.g.

pyridinylmethyl, in particular 2-pyridinylmethyl, 3-pyridinylmethyl or 4-pyridinylmethyl; or $R^9$ and $R^{10}$ together form $C_{4-6}$-alkylene.

Particularly preferred compounds of Formula I are selected from the group consisting of N-{6-[2-(4-benzyl-piperazin-1-yl)-2-oxo-ethyl]-3-hydroxy-2,2-dimethyl-chroman-4-yl}-4-ethyl-benzenesulfonamide; 4-ethyl-N-{3-hydroxy-2,2-dimethyl-6-[2-oxo-2-(4-pyridin-3-ylmethyl-piperazin-1-yl)-ethyl]-chroman-4-yl}-benzenesulfonamide; 4-ethyl-N-{3-hydroxy-2,2-dimethyl-6-[2-oxo-2-(4-pyridin-2-ylmethyl-piperazin-1-yl)-ethyl]-chroman-4-yl}-benzene-sulfonamide and 4-ethyl-N-{3-hydroxy-2,2-dimethyl-6-[2-oxo-2-(4-pyridin-4-ylmethyl-piperazin-1-yl)-ethyl]-chroman-4-yl}-benzenesulfonamide. 4-Ethyl-N-{3-hydroxy-2,2-dimethyl-6-[2-oxo-2-(4-pyridin-4-ylmethyl-piperazin-1-yl)-ethyl]-chroman-4-yl}-benzenesulfonamide is a particularly preferred compound of Formula I.

According to an embodiment of the invention, the novel compounds of Formula I are obtained by
a) reacting a compound of the general Formula II,

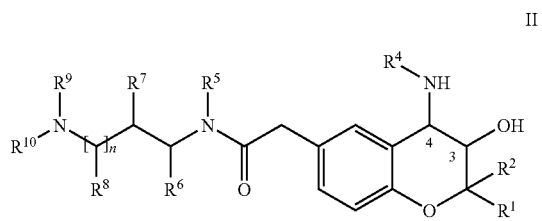

wherein $R^1$, $R^2$, $R^4$, $R^5$, $R^6$, $R^7$, $R^8$, $R^9$, $R^{10}$ and n have the above meanings, with a compound of the general Formula III,

wherein $R^3$ has the above meaning and X is a cleavable leaving group, or
b) reacting a compound of general Formula IV

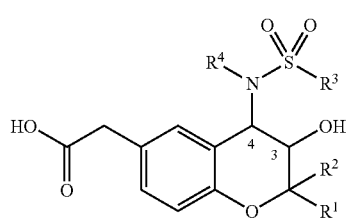

wherein $R^1$, $R^2$, $R^3$ and $R^4$ have the above meanings, with a compound of general Formula V,

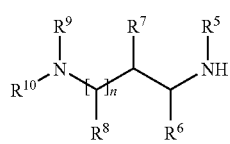

wherein $R^5$, $R^6$, $R^7$, $R^8$, $R^9$, $R^{10}$ and n have the above meanings.

The reaction according to process variant a) can be carried out using a conventional wet-chemical process in an organic solvent which is inert under the reaction conditions, in particular a dipolar-aprotic solvent such as dichloromethane or in a mixture of such solvents and in the presence of a base. Suitable bases are non-nucleophilic organic nitrogen bases such as tertiary lower alkylamines, for example triethylamine. Liquid organic bases used in excess can also be used as solvents. If desired, the reaction can be catalysed by a known coupling aid such as 4-N,N-dimethylaminopyridine (=DMAP). Suitable reaction temperatures are between room temperature and 80° C., for example 65° C. Suitable reaction pressures are between normal pressure and approximately 200 bar, for example 180 bar. If the compound of Formula III which is used is liquid, it may be advantageous to remove the solvent from the reaction mixture after the addition of the compound of Formula III to the compound of Formula II dissolved in the solvent in known manner, for example at reduced pressure. Where, in the starting compounds of Formula II, $R^4$ stands for hydrogen, it is expedient to use equimolar amounts of compound of Formula III. Usually halogen, preferably chlorine, bromine or iodine is used as leaving group X in compounds of Formula III. Furthermore, the reaction of a compound of Formula II with a compound of Formula III can also be performed in known manner on a solid phase, in particular on a reactive resin such as aminomethyl polystyrene (AMPS). This reaction variant can preferably be used for the preparation of smaller amounts of substance, for example on a scale of 1 to 10 mmol. Where synthesis is on a solid phase, preferably a readily filterable base such as known polymer-supported methylpiperidine (=PS methylpiperidine) or polymer-supported piperidine (=PS piperidine) can be used as base. Suitable reaction temperatures for solid-phase synthesis are between 10° C. and 40° C., preferably room temperature. Compounds of Formula I may be isolated in known manner from the reaction mixture and if necessary purified in known manner. Where in the compounds of Formula I $R^9$ and/or $R^{10}$ are not parts of an aromatic or heteroaromatic ring system, salt formation is possible. Suitable resulting free compounds of Formula I may thus be converted into their physiologically compatible salts, or salts of the compounds of Formula I may be converted into free compounds of Formula I.

The reaction according to process variant b) can be carried out in a manner known for aminoacylation. The carboxylic acids of Formula IV or their reactive derivatives such as acid halides, in particular acid chlorides or acid bromides, may be used as acylation agents. If the acids of Formula IV themselves are used as acylation agents, the reaction thereof with the amino compounds of Formula V can expediently also be carried out in the presence of one or more of known coupling reagents for aminoacylation reactions, for example 1,1-carbonyldiimidazole; ethyl chloroformate; N-hydroxybenzotriazole (=HOBT); an alkyl carbodiimide, e.g. N'-(3-dimethylaminopropyl)-N-ethyl-carbodiimide (=EDC) or N,N'-Diisopropylcarbodiimide (=DIC), or a cycloalkyl carbodiimide such as dicyclohexylcarbodiimide. The acylation may take place in an organic solvent which is inert under the reaction conditions at temperatures from −30° C. to +50° C., preferably at room temperature. Suitable solvents are halogenated hydrocarbons such as dichloromethane or cyclic ethers such as tetrahydrofuran or dioxane or mixtures of these solvents.

Physiologically compatible salts of the compounds of Formula I are their conventional salts with inorganic acids, for example sulphuric acid, phosphoric acids or hydrohalic acids, preferably hydrochloric acid; or with organic acids, for example lower aliphatic monocarboxylic, dicarboxylic or tricarboxylic acids such as maleic acid, fumaric acid, lactic acid, tartaric acid, citric acid; or with sulphonic acids, for example lower alkanesulphonic acids such as methanesulphonic acid or trifluoromethanesulphonic acid, or benzenesulphonic acids optionally substituted in the benzene ring by halogen or lower alkyl, such as p-toluenesulphonic acid. The hydrochloric acid salt of the compounds of Formula I are preferred.

Compounds of Formula II are novel compounds which are advantageously suitable as intermediate products for the preparation of novel pharmacologically active substances, for example for the preparation of the compounds of Formula I.

Compounds of Formula II wherein $R^4$ stands for hydrogen, can be prepared in known manner by cleaving off in acidic media any present protective group $PG^1$ from a compound of the general Formula VI,

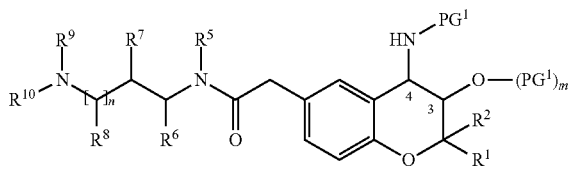

VI wherein $R^1$, $R^2$, $R^5$, $R^6$, $R^7$, $R^8$, $R^9$, $R^{10}$ and n have the above meanings, $PG^1$ stands for an amino protective group which can be cleaved off in acidic media, preferably tert.-butoxycarbonyl (=boc), and m is 0 or 1. The cleavage of the protective group can for example be accomplished by adding an acid like a mineral acid, preferably hydrochloric acid, e.g. a 4M hydrochloric acid, to the compound of Formula VI. The acid can be dissolved in a polar-protic solvent like dioxane. When in compounds of Formula VI or any compound containing protective groups $PG^1$ and mentioned hereinafter m is 0, then the substituent in 3-position of the pyran ring is meant to be hydroxy in each case.

Suitable protective groups $PG^1$ or other protective groups mentioned in this application are known in the art and can routinely be selected by a person skilled in the art, e.g. from T. W. Greene, P. G. M. Wuts, Protective Groups in Organic Synthesis, John Wiley & Sons, in its latest edition.

Where compounds of Formula I are desired wherein $R^4$ stands for $C_{1-6}$-alkyl or $C_{3-7}$-cycloalkyl-$C_{1-4}$-alkyl, a compound of Formula I wherein $R^4$ is hydrogen, or a precursor compound to a compound of Formula I, wherein $R^4$ is hydrogen, namely a precursor compound of Formula II or IV, can be alkylated in known manner. The alkylation can be carried out in particular as an aminoalkylation, by first reacting the compound of Formula I, II, or IV, wherein $R^4$ stands for hydrogen in each case, with an aldehyde of the general Formula VII, $$R^{401}\text{—CHO} \qquad \text{VII}$$

wherein $R^{401}$ is hydrogen, $C_{2-5}$-alkyl or $C_{3-7}$-cycloalkyl-$C_{0-3}$-alkyl, and then reducing the resulting imine intermediate product by addition of a reducing agent to the alkylamine compound of Formula I, II or IV. Suitable reducing agents are complex borohydrides such as $NaBH_3CN$ or known polymer-supported borohydride (=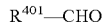$BH_4$). In a first variant, the reaction can be carried out in a polar-protic organic solvent which is inert under the reaction conditions, in particular methanol, the reduction of the imine being performed in situ without isolating it in the same solvent. Suitable reaction temperatures for this variant are between room temperature and 60° C., for example 50° C. In a second variant, the reaction of the compound of Formula I, II or IV, wherein $R^4$ stands for hydrogen, with an aldehyde of Formula V to form the imine intermediate product can be carried out in a dipolar-aprotic solvent, in particular tetrahydrofuran (=THF). In that case, it is advantageous to add catalytic amounts of a hydrophilic agent, for example an orthoester, in particular trimethyl orthoformate (=TMOF), to speed up the reaction. Then the imine intermediate product can be isolated and taken up in a polar-protic solvent stated above for the first variant, in order to perform the reduction in this solvent. This second variant may preferably be carried out at room temperature.

Compounds of Formula VI can be prepared by reacting a carboxylic acid derivative of the general Formula VIII,

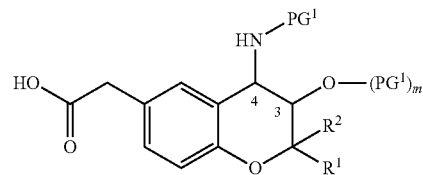

VIII wherein $R^1$, $R^2$, $PG^1$ and m have the above meanings, with an amino derivative of Formula V in a manner known for aminoacylation and described in more detail above. The carboxylic acids of Formula VIII or their reactive derivatives such as acid halides, in particular acid chlorides or acid bromides, may be used as acylation agents. If the acids of Formula VIII themselves are used as acylation agents, the reaction thereof with the amino compounds of Formula V can expediently also be carried out in the presence of one or more of known coupling reagents for aminoacylation reactions, for example 1,1-carbonyldiimidazole; ethyl chloroformate; N-hydroxybenzotriazole (=HOBT); an alkyl carbodiimide, e.g. N'-(3-dimethylaminopropyl)-N-ethylcarbodiimide (=EDC) or N,N'-Diisopropylcarbodiimide (=DIC), or a cycloalkyl carbodiimide such as dicyclohexylcarbodiimide. The acylation may take place in an organic solvent which is inert under the reaction conditions at temperatures from −30° C. to +50° C., preferably at room temperature. Suitable solvents are halogenated hydrocarbons such as dichloromethane or cyclic ethers such as tetrahydrofuran or dioxane or mixtures of these solvents.

Compounds of Formula V and compounds of Formula VII are known per se or can be prepared in known manner from known compounds.

Compounds of Formula VIII can be prepared in known manner by cleaving off in basic media any present protective group $PG^2$ from a compound of the general Formula IX,

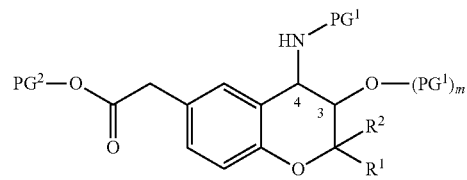

IX wherein $R^1$, $R^2$, $PG^1$ and m have the above meanings, and $PG^2$ stands for a carbonic acid protective group which can be cleaved off in basic media.

$PG^2$ in general can stand for a carbonic acid protective group which can be cleaved off in basic media or in acidic media. If $PG^2$ stands for a carbonic acid protective group which can be cleaved off in basic media, straight-chain or branched $C_{1-4}$-alkyl radicals, preferably isopropyl or methyl are suitable. Cleavage of the protective group $PG^2$, which can be cleaved off in basic media can usually be accomplished by addition of a base like an alkali hydroxide salt, e.g. lithium hydroxide. Suitable solvents in this case are water or polar-protic organic solvents like THF, or preferably mixtures of said organic solvents with water. If $PG^2$ stands for a carbonic acid protective group which can be cleaved off in acidic media, branched $C_{1-4}$-alkyl radicals, preferably tert.-butyl are suitable. The cleavage of the protective group $PG^2$, which can be cleaved off in acidic media can usually be accomplished by addition of an acid like trifluoroacetic acid. Suitable solvents are in this case polar non-protic organic solvents like toluene or xylene, or mixtures of said organic solvents.

Compounds of Formula IX can be prepared in known manner by protecting amino hydroxy chromane derivatives of general Formula X,

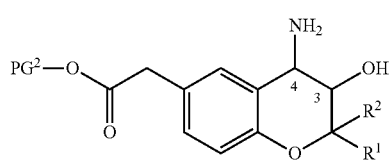

X wherein $R^1$, $R^2$ and $PG^2$ have the above meanings as given for compounds of Formula IX, with an amino protective group which can be cleaved off in acidic media, preferably the boc group. When boc-amino protected compounds of Formula X are prepared, boc-anhydride may be used as a reagent in a manner known per se. Usually, in this case a mixture of the mono-protected compound of Formula X and the di-protected compound of Formula X will be received. Typically, a 2:1 distribution will be observed in favour of the mono-protected product. Usually, the subsequent reactions to obtain compounds of Formula I and which are starting from compounds of Formula X can be performed without problems while using the mixture of protected compounds as a starting material in each case.

Compounds of Formula X can be prepared by reacting an epoxide compound of the general Formula XI,

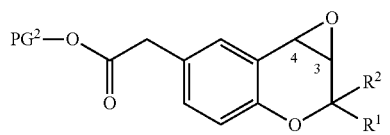

XI wherein $R^1$, $R^2$ and $PG^2$ have the above meanings as given for compounds of Formula X, in known manner with a nucleophilic organic nitrogen compound, preferably ammonia in aqueous solution like ammonium hydroxide, in a dipolar-protic solvent such as a lower-alkyl alcohol, preferably ethanol. Suitable reaction temperatures are between room temperature and 70° C.

Compounds of Formula XI can be prepared by reacting a compound of the general Formula XII,

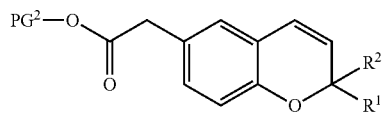

XII wherein $R^1$, $R^2$ and $PG^2$ have the above meanings as given for compounds of Formula XI, in known manner with a peroxide compound capable of epoxide formation, preferably with m-chloroperbenzoic acid (MCPBA), in an organic polar-aprotic solvent which is inert under the reaction conditions, preferably dichloromethane, and in the presence of a base. A suitable base is in particular an aqueous solution of sodium hydrogen carbonate. The reaction may preferably be carried out at room temperature.

Compounds of Formula XII can be prepared by reacting a compound of the general Formula XIII,

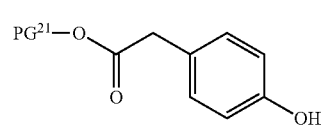

XIII wherein $PG^{21}$ has the meaning given above for $PG^2$ in compounds of Formula XII, while preferred alternatives of $PG^{21}$ are unbranched lower alkyl radicals like $C_{1-4}$-alkyl, preferably methyl, with a compound of the general Formula XIV,

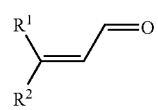

XIV wherein $R^1$ and $R^2$ have the above meanings, in known manner, and subsequently, if desired, exchanging protective groups $PG^{21}$ in known manner for any desired protective groups $PG^2$. The reaction can be carried out in an organic solvent which is inert under the reaction conditions, such as toluene or xylene and in the presence of an acid with water being separated off by azeotropic distillation. A suitable acid is for example acetic acid or propionic acid. Advantageously, operation is with the addition of a catalyst such as a Lewis acid, for example phenylboronic acid. Suitable reaction temperatures are between room temperature and the boiling point of the solvent or of the solvent mixture, for example around 120° C.

The compounds of Formula XIII and of Formula XIV are known per se or can be prepared in known manner from known compounds.

Compounds of Formula IV are novel compounds which are advantageously suitable as intermediate products for the preparation of novel pharmacologically active substances, for example for the preparation of the compounds of Formula I.

Compounds of Formula IV wherein $R^4$ stands for hydrogen, can be prepared in known manner, e.g. by cleaving off a protective group $PG^3$ from a compound of general Formula XV,

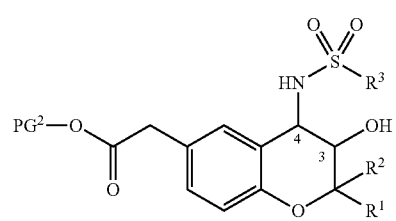

XV wherein $R^1$, $R^2$ and $R^3$ have the above meanings and $PG^2$ stands for a carbonic acid protective group which can be cleaved off in acidic media like a branched or unbranched $C_{1-4}$-alkyl radical, preferably tert.-butyl.

Compounds of Formula XV can be prepared in known manner, e.g. by reacting a compound of Formula X, wherein $PG^2$ has the above meaning as given for compounds of Formula XV, with a compound of Formula III. The reaction can be carried out as described above in process variant a) for the reaction of a compound of Formula I with a compound of Formula III.

Compounds of Formula I have at least in the vicinal carbon atoms in position 3 and in position 4 of the pyran ring in each case a chiral center and can therefore occur in several isomeric forms. The subject of the invention is both the isomerically pure compounds of Formula I and mixtures of these isomers. The optically active compounds of Formula I can be obtained for example from the mixtures of the isomers of compounds of Formula I or from mixtures of the isomers of compounds of Formula II or IV in known manner, e.g. by chromatographic separation on chiral separating materials. Mixtures of the isomers of compounds of Formula I, wherein $R^9$ and/or $R^{10}$ are not part of an aromatic or heteroaromatic ring system, or mixtures of the isomers of compounds of Formula II may also be obtained by reaction with suitable optically active acids, e.g. camphorsulphonic acid or D- or L-tartaric acid, and subsequent fractionation into the respective optical antipodes by fractional crystallisation of the salts obtained. Mixtures of the isomers of compounds of Formula IV may also be obtained by reaction with suitable optically active bases and subsequent fractionation into the respective optical antipodes by fractional crystallisation of the salts obtained. Compounds of Formula I further may have chiral centers at the carbon atoms carrying the substituents $R^5$, $R^6$, $R^7$ and/or $R^8$. Those chiral centers may be varied by selecting or synthesizing suitable compounds of Formula VIII, wherein the appropriate chiral centers are already present in a known manner.

The optically active compounds of Formula I can also partly be prepared directly by chiral synthesis. Where compounds of Formula I are to be prepared wherein the hydroxy substituent in position 3 of the pyran ring and the $R^4NSO_2R^3$-substituent in position 4 of the pyran ring are in a stereochemically defined trans position to one another, in each case the starting point may be epoxides of Formula XI wherein the appropriate stereochemistry is already predetermined. Epoxides of Formula XI with correspondingly predetermined stereochemistry can for example be prepared by epoxidising alkenes of Formula XII in known manner with the aid of a chiral catalyst, e.g. (S,S)-(+)-N,N'-bis(3,5-di-tert.-butylsalicylidene)-1,2-cyclohexanediaminomanganese (III) chloride (="Jacobsen's catalyst"; "(S,S)-manganese (III) salen") in accordance with the method of Jacobsen (cf. e.g. WO 91/14694 A1). Where for example a compound of Formula I is to be prepared wherein the chiral center in position 3 of the pyran ring is in the S configuration and wherein the chiral center in position 4 of the pyran ring is in the R configuration, an intermediate product of Formula XII can be reacted in the presence of a chiral catalyst, in particular (S,S)-manganese (III) salen and in the presence of an oxygen donor, in particular sodium hypochlorite in aqueous solution, in an organic solvent which is inert under the reaction conditions, in particular dichloromethane. Expediently, the reaction is carried out at a pH value between 9.5 and 11.5. To set a suitable pH value, preferably a buffer consisting of $Na_2HPO_4$ and pyridine-N-oxide can be added to the reaction mixture. Suitable reaction temperatures are between $-10°$ C. and room temperature, preferably at $0°$ C. Where a compound of Formula I is to be prepared wherein the chiral center in position 3 of the pyran ring is in the R configuration and wherein the chiral center in position 4 of the pyran ring is in the S configuration, the procedure can be analogous to the directions described above, but "(R,R)-manganese (III) salen" is then used instead of (S,S)-manganese (III) salen.

In the nucleophilic ring-opening reaction of epoxides of Formula XI described above in two variants, as a rule compounds of Formula X are obtained wherein the vicinal substituents in position 3 and in position 4 of the pyran ring, namely the hydroxyl group and the amino group, are each in the trans position to one another.

The advantageous effects of compounds of Formula I as pharmacologically active active substances will become apparent from the following background: it is already known that substances which block endogenous cardiac potassium channels can be used as active substances to counter cardiovascular diseases, in particular to counter cardiac arrhythmias. By blocking outward-directed potassium currents in the heart, a prolongation of the action potential of the heart can be brought about which has a beneficial effect on antiarrhythmic heart conditions. Examples of this known treatment are Class III antiarrhythmic drugs. One problem of such non-specific potassium channel blockers is their low degree of selectivity with respect to their effect on different heart tissues. Thus for a relatively long time it has been assumed that in particular Class III antiarrhythmic drugs can lead to undesirable prolongation of the QT interval in the electrocardiogram (=ECG) and to polymorphic ventricular tachycardias ("torsades de pointes"), by means of which ultimately undesirable complications such as for example ventricular fibrillation can be triggered. For this reason, potassium channel blockers have been sought which are capable of selectively influencing the potassium currents of the atrium, but not of the ventricle. Since the $K_v1.5$-potassium channels in the heart which were discovered some time ago are located exclusively in the atrium, but not in the ventricle, it can be assumed that these $K_v1.5$-potassium channel-blocking compounds are suitable as atrial-selective antiarrhythmic drugs. $K_v1.5$-potassium channels and other potassium channels are however located not only in the heart, but e.g. also in vessels of the body. Therefore it cannot always be ruled out that $K_v1.5$-potassium channel-blocking compounds may lead to increases in blood pressure owing to the blockade of potassium channels in the vessels. $K_v1.5$-potassium channel-blocking compounds which are free of side-effects which raise blood pressure are therefore preferred. Further undesirable side-effects which may occur on administration of many $K_v1.5$-potassium channel-blocking compounds are additional Class I-antiarrhythmic side-effects and also negatively inotropic effects.

The compounds of Formula I are distinguished by an effect which particularly pronouncedly and selectively blocks the cardiac $K_v1.5$-potassium channels. In addition to particularly good effectiveness and a marked atrial-selective antiarrhythmic action profile, the compounds of Formula I at most have slight undesirable side-effects such as increase in blood pressure, Class I -antiarrhythmic side-effects and negatively inotropic effects. The compounds of Formula I are therefore indicated for the treatment and/or prophylaxis of cardiovascular diseases, in particular atrial fibrillation, atrial flutter and other cardiac arrhythmias, in larger mammals and humans.

Compounds of Formula I are further characterized by their comparatively high water-solubility, in particular those compounds of Formula I, wherein the substituent $R^{10}$ has the meaning $C_{1-6}$-alkyl; phenyl-$C_{1-4}$-alkyl or pyridinyl-$C_{1-4}$-alkyl, the nitrogen atom directly bonded to $R^{10}$ thus not being part of an aromatic or heteroaromatic ring system. Improved water-solubility is expected to lead to improved bioavailability, thus facilitating pharmaceutical formulations with a reduced amount of or even without the need for using organic solvents and/or solubility enhancers.

Furthermore, the compounds of Formula I exhibit a clear effect of blocking the $K_v1.3$-potassium channels. $K_v1.3$-potassium channels are preferentially located in cells of the immune system. A connection is made between blockade of the $K_v1.3$-potassium channels and inter alia an anti-proliferative and/or immunosuppressive effect (cf. C. Beeton et al., The Journal of Immunology 166 (2001) 936-944). It can therefore be assumed of compounds which are capable of blocking $K_v1.3$-potassium channels—for example the present compounds of Formula I—that they are also suitable for the treatment and/or prophylaxis of proliferative, chronic inflammatory and autoimmune diseases. Autoimmune diseases in this regard may comprise e.g. addison's disease, alopecia areata, ankylosing, spondylitis, antiphospholipid syndrome, autism, autoimmune atherosclerosis, autoimmune diabetes, insipidus, autoimmune endometriosis, autoimmune eye diseases, autoimmune hemolytic anemia, autoimmune hemophilia, autoimmune hepatitis, autoimmune interstitial cystitis, autoimmune lymphoproliferative syndrome, autoimmune myelopathy, autoimmune myocarditis, autoimmune neuropathies, autoimmune oophoritis, autoimmune orchitis, autoimmune thrombocytopenia, autoimmune thyroid diseases, autoimmune urticaria, autoimmune uveitis, autoimmune vasculitis; Behcet's disease, Bell's palsy, bullous pemphigoid; Celiac disease, chronic fatigue syndrome, Crohn's disease; dermatitis herpetiformis, dermatomyositis, discoid lupus erythematosus; Goodpasture syndrome, Graves disease, Guillain-Barre syndrome, Hashimoto's thyroiditis, herpes gestationis, Huntington's disease, IgA nephropathy, immune thrombocytopenic, purpura interstitial cystitis; lupus lyme disease; Miller Fisher syndrome, mixed connective tissue disease; multiple sclerosis, myasthenia gravis; paraneoplastic autoimmune syndromes, pemphigus foliaceus, pemphigus vulgaris, pernicious anemia, Peyronie's disease, polyendocrine deficiency syndrome, primary biliary cirrhosis, primary glomerulonephritis, primary sclerosing cholangitis, psoriasis, psoriatic arthritis; Rasmussen's encephalitis, relapsing polychondritis, rheumatoid arthritis; sarcoidosis, scleroderma, Sjogren's syndrome, Stiff-Person syndrome; Sydenham chorea, sympathetic ophthalmitis, temporal arteritis, type 1 diabetes, ulcerative colitis; vitiligo; Wegener's granulomatosis. Furthermore, a connection is made between blockade of the $K_v1.3$-potassium channels and metabolic diseases (cf. J. Xu et al., Human Molecular Genetics 2003 Vol. 12 No. 5, 551-559). It can therefore be assumed of compounds which are capable of blocking $K_v1.3$-potassium channels—for example the present compounds of Formula I or the compounds as disclosed in published international patent application WO 2005/037780 (=US 2005/0148659)—that those compounds may also be suitable for the treatment and/or prophylaxis of metabolic disorders or diseases such as central obesity; hypertension, in particular arterial hypertension; insulin resistance, in particular diabetes mellitus type II; glucose intolerance or impaired glucose tolerance; dyslipoproteinaemia, in particular as hypertriglyceridaemia, accompanied by dyslipoproteinaemia occurring with lowered HDL-cholesterol; and hyperuricaemia.

Beneficial effects may also be anticipated if the aminoalkyl-amidomethyl-substituted 2-(4-sulphonylamino)-3-hydroxy-3,4-dihydro-2H-chromen-6-yl derivatives of the present invention or the amidomethyl-substituted 2-(4-sulphonylamino)-3-hydroxy-3,4-dihydro-2H-chromen-6-yl derivatives as disclosed in WO 2005/037780 are administered in combination (either fixed combination or subsequently in either order) with at least one other cardiovascular active drug compound selected from alpha-adrenoceptor antagonists (non-selective), e.g. tolazoline or phenoxybenzamine; alpha-adrenoceptor antagonists (selective), e.g. doxazosin (mesylate), prazosin (hydrochloride) (and polythiazide), terazosin (hydrochloride) or urapidil;

alpha2-adrenoceptor agonists (including centrally acting alpha2-adrenoceptor agonists), e.g. clonidine, guanfacine, guanabenz, methyldopa and moxonidine;

anti-anginal drugs, e.g. bepridil, beta blockers, diltiazem, nicardipine, nifedipine, nitrates; anticoagulants, e.g. dalteparin, danaparoid, enoxaparin, heparin, tinzaparin, warfarin;

antiplatelet drugs, e.g. abciximab, aspirin, aspirin and dipyridamole (Aggrenox), cilostazol, clopidogrel, dipyridamole, eptifibatide, ticlodipine, tirofiban;

antiarrhythmic drugs like class I antiarrhythmics, e.g. sodium channel blockers, disopyramide, flecainide, lidocaine, mexiletine, moricizine, procainamide, propafenone, quinidine, tocainide; or class II antiarrhythmics, e.g. beta blockers, acebutolol, atenolol, betaxolol, bisoprolol, carvedilol, esmolol, metoprolol, nadolol, propranolol, sotolol, timolol; or class III antiarrhythmics, e.g. potassium channel blockers, amiodarone, azimilide, bepridil, dofetilide, ibutalide, sotalol, tedisamil; or class IV antiarrhythmics, e.g. calcium channel blockers, diltiazem, verapamil;

beta-adrenoceptor antagonists (beta blockers) e.g. acebutolol, alprenolol, atenolol, betaxolol, bisoprolol, bupranolol, carazolol, carteolol, celiprolol, mepindolol, metipranolol, metoprolol, nadolol, oxprenolol, penbutolol, pindolol, propranolol, sotalol and timolol;

calcium channel blocking agents (=calcium antagonists) e.g. amlodipine, bepridil, felodipine, isradipine, nicardipine, nifedipine, nilvadipine, nimodipine, nisoldipine, nitrendipine; gallopamil, verapamil; diltiazem and fendiline;

diuretics, e.g. adenosine A1 antagonists, thiazide diuretics, thiazide analogues, loop diuretics, potassium sparing diuretics, carbonic anhydrase inhibitors and/or ethacrynic acid. Suitable adenosine A1 antagonists can be selected from the group comprising 1,3-dipropyl-8-cyclopentylxanthine (DPCPX); 4-[(2-phenyl-7H-pyrrolo[2,3-d]pyrimidin-4-yl)amino]-trans-cyclohexanol; (4S)-4-hydroxy-1-(2-phenyl-7H-pyrrolo[2,3-d]pyrimidin-4-yl)-L-prolinamide; 8-cyclopentyl-3-N-[3-((3-(4-fluorosulphonyl)benzoyl)-oxy)-propyl]-1-N-propyl-xanthine (FSCPX); BG-9928 (CAS No. 340021-17-2); CPX (CAS No. 102146-07-6); FK-352 (CAS No. 143881-08-7); FK-453 (CAS No. 121524-18-3); FK-838 (CAS No. 131185-37-0); FR-166124 (CAS No. 171050-45-6); KW-3902 (CAS No. 136199-02-5); N-0861 ([+/−]N6-endo-norbornan-2-yl-9-methyl-adenine, CAS No. 141696-90-4); WRC-0342 (CAS No. 175097-37-7); WRC-0571 (8-(N-methylisopropyl)amino-N6-(5'-endohydroxy-endonorbornyl)-9-methyladenine, CAS No. 175097-35-5); naxifylline (CAS Nos. 166374-48-7 and 166374-49-8) or any physiologically compatible tautomers, salts, solvates, prodrugs or esters thereof. Suitable thiazide diuretics can be selected from the group comprising althiazide, bemetizide, bendroflumethiazide, benzylhydrochlorothiazide, benzthiazide, buthiazide, chlorothiazide, cyclothiazide, cyclopenthiazide, ethiazide, hydrochlorothiazide, hydroflumethiazide, methylclothiazide, paraflutizide, polythiazide, teclothiazide, trichlormethiazide or any physiologically compatible tautomers, salts, solvates, prodrugs or esters thereof. Suitable thiazide analogue diuretics can be selected from the group comprising chloraminofenamide, chlortalidone, clofenamide, clopamide, clorexolone, fenquizone, indapamide, mefruside, metolazone, quinethazone, tripamide and xipamide. Suitable loop diuretics can be selected from the group comprising azosemide, bumetanide, furosemide, piretanide, torsemide or any physiologically compatible tautomers, salts, solvates, prodrugs or esters thereof. Suitable potassium sparing diuretics can be selected from the group consisting of amiloride, potassium canrenoate, spironolactone, triamterene or any physiologically compatible tautomers, salts, solvates, prodrugs or esters thereof. Suitable carbonic anhydrase inhibitor diuretics can be selected from the group consisting of acetazolamide, brinzolamide, dichlorophenamide, dorzolamide, ethoxzolamide, indisulam, methazolamide, zonisamide or any physiologically compatible tautomers, salts, solvates, prodrugs or esters thereof; or from mixed antagonists of alpha- and beta-adrenoceptors, e.g. carvedilol or labetolol. Miscellaneous adenosine, digoxin.

Description of the Pharmacological Test Methods

The example numbers quoted relate to the preparation examples described below.

1. In-Vitro Investigation of the $K_v1.5$-Potassium Channel-Blocking Effect of the Substances The $K_v1.5$-potassium channel-blocking effect of the substances is demonstrated in a known test model or analogously to this test model (cf. W. Hu et al., J. Pharmacol. Toxicol. Methods 34 (1995) 1-7). In this test model, a cell line of egg cells of the Chinese hamster (="Chinese hamster ovary cells", "CHO") is used which originates from a single cell and stably expresses the $K_v1.5$-channel. By incubation overnight in a nutrient medium containing RbCl or a "loading buffer" (all values in mM: RbCl 5, NaCl 140, $CaCl_2$ 2, $MgSO_4$ 1, HEPES buffer 10, glucose 5) the aforementioned ovary cells are loaded with $Rb^+$ under the influence of $Na^+/K^+$-ATPase. Thereafter, a portion of the ovary cells is incubated as a reference standard in the absence of an inhibitor, while another portion of the ovary cells is incubated in the presence of the respective inhibitory test substance of Formula I. Then the ovary cells are depolarised by increasing the extracellular potassium-ion concentration, which causes the $K_v1.5$-potassium channels of the ovary cells to open. In the absence of an inhibitor, the $Rb^+$ ions flow through the $K_v1.5$-potassium channels into the liquid surrounding them. In the presence of an inhibitory test substance of Formula I, on the other hand, the $Rb^+$ ions remain locked within the ovary cells. The extent of the $K_v1.5$-potassium channel-blocking effect of the test substances of Formula I is determined by measuring the $Rb^+$ ion concentration in the liquid surrounding them by means of atomic absorption spectroscopy against a reference standard.

Chinese hamster ovary cells (see above) were cultivated in a known, RbCl-containing nutrient medium for CHO-cells and placed in the sample wells of a 96-sample capacity sample plate ("96 well plate"). The ovary cells were allowed to grow overnight in order to obtain monolayers of the ovary cells. Then first of all the nutrient medium was pipetted off and each sample well was washed three times with 100 μl each time of a preincubation buffer of low potassium-ion concentration (all values in mM: KCl 5, NaCl 140, $CaCl_2$ 2, $MgSO_4$ 1, HEPES buffer 10, glucose 5). Then 50 μl of a solution of the respective test substance (stock solution in DMSO, dilution with preincubation buffer, final concentration in the test batch 10 μM) or of the solvent (as negative controls) was added to each sample well and incubated for 10 min. in each case at room temperature. Then 50 μl of a stimulation buffer with elevated potassium-ion concentration (KCl 145 mM, NaCl 0 mM, otherwise as preincubation buffer) was added to each sample well and the samples were then incubated for a further 10 min. at room temperature. In each case, 80 μl of the liquid surrounding the ovary cells from each sample well was then transferred separately to the sample wells of an analysis sample plate, and the $Rb^+$ ion concentration in the liquids was determined by atomic absorption spectroscopy. The test substances were each double-tested. The signal section which represented the $K_v1.5$ component of the $Rb_+$ outflow was defined by using as positive control the known potassium channel blocker 4-AP in a high concentration ($100 \times IC_{50}$ for the $K_v1.5$ channel). This made it possible to determine which portion of the $Rb_+$ outflow was dependent on the influence of the 4-AP and therefore is to be assigned to the $K_v1.5$ channel. For the substances which in the concentration of 10 μM used led to a reduction in the $Rb_+$ outflow of at least 50%, additional tests were performed with lower concentrations of the test substances in order to be able to determine the half-maximum effective concentration. In each case the concentration of half-maximum inhibition of the test substances of Formula I ($IC_{50}$) was given as characteristic variable.

In this test model the test substances of Formula I listed in Table 1 below had the $IC_{50}$ values given below:

TABLE 1

| $K_v1.5$-potassium channel-blocking effect of the test substances in vitro | |
|---|---|
| Example No. | $IC_{50}$ |
| 1 | 5.8 |
| 2 | 5.5 |
| 3 | 5.7 |
| 4 | 5.6 |
| 5 | 5.8 |
| 6 | 6.0 |
| 7 | 5.7 |
| 10 | 9.5 |

2. In-Vitro Investigation of the $K_v1.3$-Potassium Channel-Blocking Effect of the Substances The Kv1.3-potassium channel-blocking effect of the substances is demonstrated in a known test model (e.g. from Genion, Hamburg) or analogously to this test model (cf. J. Plásek and K. Sigler, J. Photochem. Photobiol. 33 (1996) 101-124). In this test model, known ovary cells of the Chinese hamster (=CHO) are used which are stably transfected with the Kv1.3-potassium channel. The blockade of the cell-inherent Kv1.3-potassium channel activity in the transfected cells is accompanied by a positive shift in the membrane potential from approx. −40 mV to −30 mV, whereas in the wild-type CHO cells investigated in parallel no significant shift in the membrane potential is triggered. A change in the membrane potential is thus connected to the reduction in the Kv1.3-potassium channel activity. By blocking the Kv1.3-potassium channels e.g. with substances of Formula I and the resulting change in the membrane potential, an accumulation of a membrane potential-sensitive fluorescent dye in intracellular compartments of the ovary cells and ultimately increasing fluorescence occurs. The change in the membrane potential of the ovary cells is therefore measured indirectly via the increase in fluorescence of the membrane potential-sensitive dyes.

The cells were transfected with the Kv1.3 plasmid in known manner with a commercially obtainable transfection reagent (DMRIE-C from Gibco BRL, Germany). The successful transfection was verified by means of immunofluorescence and by "patch-clamp" investigations of the potassium ion current. The fluorescence measurements were performed on a Tecan Safire fluorescence reader from Tecan, Germany. In each case, the increase in the fluorescent intensity caused by the blockade of the Kv1.3-potassium channels in the ovary cells with substances of Formula I in a concentration of 10 µM was determined as characteristic variable. The increase in the fluorescent intensity was given in each case in percent (%) compared with an increase in the fluorescent intensity caused by the reference substance margatoxin. Margatoxin is known as a selective Kv1.3-potassium channel blocker (see e.g. M. Garcia-Calvo et al., J. Biol. Chem. 268 (1993) 18866-18874).

In this test model the test substances of Formula I listed in Table 2 below had the percentages given below:

TABLE 2

Kv1.3-potassium channel-blocking effect of the test substances in vitro

| Example No. | Increase in the fluorescent intensity (% margatoxin) |
|---|---|
| 4 | 41.8 |
| 5 | 39.8 |
| 6 | 59.9 |

3. Investigation of the Functional Effectiveness of the Substances on the Atrium of Rats' Hearts In Vitro The functional antiarrhythmic effectiveness of the substances is demonstrated in the test model set forth below. In this test model it is determined to what extent the $K_v1.5$-blocking substances of Formula I result in a prolongation of the functional refractory period in the left atrium of rats. The refractory period is the minimum possible elapsed time between the basic stimulus and additional stimulus in which a renewed contraction can be triggered. The extent of the prolongation of the functional refractory period is a measurement of the antiarrhythmic effectiveness of the substances according to the invention. The functional refractory period is determined by testing on the electrically stimulated preparation at what elapsed time from the preceding contraction a renewed contraction can be triggered by additional electrical stimuli.

The hearts were removed from freshly sacrificed rats (Sprague-Dawley, Charles-River, Germany). The left atria were isolated and fastened to force transducers in a temperature-controlled (30° C.), gasified ($O_2$ 95%, $CO_2$ 5%) organ bath which was filled with modified Tyrode solution (all values in mM: NaCl 137; KCl 2.7; $CaCl_2$ 1.8; $MgCl_2$ 0.8; $NaHCO_3$ 11.9; $NaH_2PO_4$ 0.6; glucose 5). In order to trigger regular contractions, the preparations were electrically stimulated (rectangular pulses, pulse magnitude 3.5× threshold stimulus, pulse width 1.5 ms, frequency 1 Hz). Initially, the initial value of the functional refractory period was determined by applying extra pulses in addition to the basic stimulus, the elapsed time from the preceding basic stimulus being shortened until no further additional contraction could be triggered. Then the cumulative addition of increasing concentrations (0.1-32 µM) of the substances of Formula I took place at intervals of 20 min. each, the refractory period being determined again in each case 18 min. after the addition had taken place. Before the measurement, stock solutions of the test substances (3.2 and 0.32 mM in 100% DMSO) were prepared. In order to achieve the desired final concentrations of the substances (0.1-32 µM) in the organ bath (volume 25 or 100 ml), corresponding volumes of these stock solutions were then poured into the organ bath.

In each case the prolongation of the functional refractory period (FRP) in the left atrium of the rats' hearts in milliseconds observed after the addition of 10 or 32 µM of the respective substance of Formula I to the atrial preparations was given as characteristic variable.

In this test model the test substances of Formula I listed in Table 3 below exhibited the prolongations of refractory period given below, higher values representing a stronger antiarrhythmic effectiveness:

TABLE 3

FRP-prolonging effect of the test substances (10 µM or 32 µM) on the left atria of rats' hearts in vitro

| Example No. | FRP prolongation [ms] |
|---|---|
| 1 | 15 (10 µM) |
| 3 | 15 (10 µM) |
| 6 | 16 (32 µM) |
| 7 | 13 (10 µM) |
| 8 | 22 (32 µM) |
| 10 | 24 (10 µM) |
| 11 | 20 (32 µM) |
| 12 | 22 (32 µM) |

4. Investigation of the Functional Effectiveness of the Substances on Guinea-Pig Hearts In Vivo In the test model shown below, it is shown that the substances according to the invention at most have slight undesirable proarrhythmic effects on repolarisation in the ventricle. To this end, the influence of the compounds of Formula I on the effective refractory period (ERP) and other influencing variables on guinea-pig hearts in vivo were investigated. In this test model, non-selective potassium channel blockers not in accordance with the invention, which also block HERG and/or $K_v$LQT1 channels, result in undesirable prolongation of the ERP and the QT time on an electrocardiogram (=ECG). The QT time is likewise a measurement of the repolarisation in the heart. Prolongations of the ERP and the QT time which are due to the substances are both each independently interpreted as indications of the risk of undesirable torsade-de-pointes arrhythmias occurring. Furthermore, also in each case the QRS interval was determined from the ECG as a measurement of the velocity of spread of stimulus in the ventricle. Even a prolongation of the QRS interval caused by a test substance is connected with an increased risk of undesirable pro-arrhythmic side-effects. Therefore in this test model the lack of an ERP and QT time prolongation signifies a low risk, but the occurrence of a relevant ERP and QT prolongation on the other hand signifies an elevated risk of undesirable pro-arrhythmic effects. Also the lack of a prolongation of the QRS interval which is due to the substances due to the substances of Formula I investigated designates a low risk of undesirable pro-arrhythmic side-effects, since lack of QRS prolongation indicates an undisturbed spread of stimulus in the ventricle. Conversely, a QRS prolongation, which is typically triggered by Class I antiarrhythmic drugs indicates slowing of the conduction velocity and may promote the occurrence of ventricular tachycardias to ventricular fibrillation.

Male guinea pigs (Dunkin-Hartley from Charles River) were anaesthetized (ketamine 50 mg/kg, xylazine 10 mg/kg) and each of them was provided with a venous access via one jugular vein for administration of compounds of Formula I or a vehicle. A bipolar stimulation catheter was fed into the right ventricle of the guinea pigs via the other jugular vein (stimulation frequency 5 Hz). The arterial blood pressure was measured by a catheter located in the carotid artery which was connected to a Statham pressure transducer. The ECG was recorded via needle electrodes. The measured data were digitised via an A/D converter, and recorded on a computer with suitable software (Ponemah Physiology Platform from Gould, USA). After an equilibration period of 45 min., increasing doses of the compounds of Formula I or of the vehicle were administered intravenously (=i.v.) to the guinea pigs at 12-minute intervals. Before the first administration and in each case one minute after administration of increasing doses (0.1-max. 30 µmol/kg) of the substances of Formula I, the effective refractory period was measured. For this, after five normal stimuli in each case an additional pulse was applied and the elapsed time thereof from the preceding pulse was increased until a heart action was triggered. The observed time interval corresponds to the ERP of the ventricular myocardium.

In order to detect possible effects of the test substances on the blood pressure, in the same test model after each administration of substance the systolic and diastolic blood pressure was determined and compared with the previous blood-pressure level. The parameters were recorded automatically 1 and 8 min after each administration of substance. Table 4 furthermore shows the changes in systolic blood pressure due to the compounds of Formula I given below (minus effects due to the vehicle). None of the compounds listed resulted in a relevant increase in blood pressure.

In this test model, the test substances of Formula I listed in Table 4 below had the effects given below. Only statistically significant effects were listed, with a t-test with a significance limit of P<0.05 being used for the statistical testing. In Table 4 below, the indication "n.s." (="not statistically significant") means that the substance of the corresponding example does not have any statistically significant influence on the measured variable listed.

TABLE 4

Effect of the test substances (1 min. after administration of 10 or 30 µmol/kg i.v.) on the ERP, QT and QRS intervals in the ventricle of guinea pigs and simultaneously measured changes in the systolic blood pressure in vivo (n.s. = not statistically significant, negative values indicate shortening or reduction)

| Ex. No. | ERP (ms) | QT (ms) | QRS (ms) | syst. blood pressure (mmHg) |
|---|---|---|---|---|
| 8** | n.s. | n.s. | n.s. | −17.0 |
| 10* | n.s. | n.s. | n.s. | −10.7 |
| 11** | n.s. | n.s. | n.s. | −15.6 |
| 12** | n.s. | 6.3 | n.s. | −24.2 |

*10 µmol/kg i.v.;
**30 µmol/kg i.v.

The particularly good compatibility of the compounds according to the invention can also be demonstrated in further pharmacological test models. Thus for example it can be demonstrated in an in vitro test on cardiac muscle preparations of guinea pigs that the compounds of Formula I at most have slight Class I-antiarrhythmic side-effects. Furthermore, it can be demonstrated in an in vitro model on rats' hearts and in another in vitro model on guinea pigs' hearts that the compounds of Formula I at most cause slight negatively inotropic effects.

The compounds of Formula I may be administered in conventional pharmaceutical compositions. In an individual case, special dosage forms may be indicated. The doses to be used may vary individually and will naturally vary according to the type of condition to be treated and the substance used. In general, however, medicinal forms with an active substance content of 0.2 to 500 mg, in particular 10 to 200 mg, active substance per individual dose are suitable for administration to humans and larger mammals.

The compounds may be contained according to the invention, together with conventional pharmaceutical auxiliaries and/or carriers, in solid or liquid pharmaceutical compositions suitable for administration. Said pharmaceutical compositions may be produced by means of usual processes using auxiliary substances such as liquid or solid carrier material. Types of pharmaceutical compositions that may be used are apparent to a person skilled in the art from the specification and/or general knowledge in the art.

Examples of solid compositions are tablets, including coated tablets, microtablets and chewable tablets; capsules, including microcapsules; powders or granules; suppositories or ointments, including creams and gels. For the preparation of solid medicament forms, the active substances may for example be mixed with the auxiliaries and/or carriers in conventional manner and may be wet or dry granulated. The granules or powders may be poured directly into capsules or be pressed into tablet cores in conventional manner. These may be coated in known manner if desired.

Liquid compositions such as solutions, parenteral solutions, suspensions or emulsions of the active substances may contain the usual diluents such as water, oils and/or suspension agents such as polyethylene glycols and the like. Other auxiliaries may additionally be added, such as preservatives, taste correctives and the like.

The pharmaceutical compositions of the invention may thus be administered in either solid or liquid form, e.g. enterally, orally, parenterally (intramuscularly or intravenously), rectally or locally (topically). Suitable excipients for such formulations are the pharmaceutically customary liquid or solid carriers, fillers and extenders, solvents, emulsifiers, lubricants, tablet disintegrating agents, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. In embodiments of the invention, a pharmaceutical pack or kit is provided comprising one or more container(s) filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

The following examples are intended to explain the invention further, without limiting its scope.

EXAMPLE 1

(3S,4R)—N-{6-[2-(4-Benzylpiperazin-1-yl)-2-oxo-ethyl]-3-hydroxy-2,2-dimethylchroman-4-yl}-4-n-propylbenzenesulfonamide

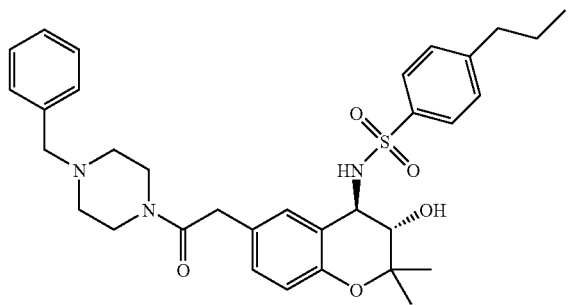

A) A 5 liter flange flask was charged with methyl 4-hydroxyphenylacetate (175.6 g), phenyl boronic acid (128.9 g) and m-xylene (3.5 liters). To this mixture was added 3-methylbut-2-enal (88.9 g) and glacial acetic acid (130 ml). The resulting mixture was heated at 140° C. under nitrogen using a Dean-Stark apparatus. The reaction was monitored by HPLC-MS (High-Performance Liquid Chromatography-Mass Spectrum) and stopped when no further progress could be observed (approximately 72 hours). Following this the reaction mixture was cooled to room temperature, filtered and the solvent removed in vacuo. The residue was dissolved in 1:1 v/v (volume by volume) THF/ammonium hydroxide and stirred for 2 h.

The THF was removed in vacuo and ethyl acetate added. The organic layer was separated and washed with 1M (1 molar) sodium hydroxide, brine, dried over $Na_2SO_4$ and the solvent removed in vacuo. The crude product (155 g) was purified by dry flash column chromatography using gradient elution 15:1 to 10:1 v/v (volume by volume) hexane/ethyl acetate to give 106 g of 2,2-dimethyl-2H-chromen-6-yl)acetic acid methyl ester.

$^1$H-NMR (δ ppm, $CDCl_3$): 7.00 (dd, 1H, J=8.16, 2.32 Hz), 6.89 (d, 1H, J=2.32 Hz), 6.72 (d, 1H, J=8.24 Hz), 6.29 (d, 1H, J=9.80 Hz), 5.60 (d, 1H, J=9.80 Hz), 3.69 (s, 3H), 3.51 (s, 2H), 1.42 (s, 6H).

HPLC-MS (ES+, 10 eV): 233.25(M+, 10%), 173.16 ([M-$C_2H_3O_2$]$^+$, 100%).

B) A 1 liter flask was charged with (2,2-dimethyl-2H-chromen-6-yl)acetic acid methyl ester (for preparation see above) (50 g), 500 ml of isopropanol and Ti(OEt)$_4$ (0.7 equivalents; eq.). The resulting solution was heated at reflux for 16 h. The reaction was monitored by combined liquid chromatography/mass spectroscopy (=LCMS) and stopped when the reaction was complete. After conversion of all the starting material (formation of 5% of ethyl ester) the reaction mixture was cooled to room temperature. Water (50 ml) was added dropwise and the solvent was removed in vacuo. The resulting solid was filtered and washed with ethyl acetate. The solution of ethyl acetate was filtered through silica and evaporated in vacuo to give 56 g of (2,2-dimethyl-2H-chromen-6-yl)acetic acid isopropyl ester which was used in the next step without further purification.

$^1$H-NMR (δ ppm, $CDCl_3$): 7.00 (dd, 1H, J=8.08, 2.20 Hz), 6.89 (d, 1H, J=1.96 Hz), 6.71 (d, 1H, J=8.08 Hz), 6.28 (d, 1H, J=9.76 Hz), 5.60 (d, 1H, J=9.80 Hz), 5.00 (septet, 1H, J=6.12 Hz), 3.46 (s, 2H), 1.42 (s, 6H), 1.22 (d, 6H, J=6.12 Hz).

HPLC-MS (ES+): 261.03 ([M+H]$^+$, 11%), 218.91 ([M-$C_3H_7$]$^+$, 100%), 172.84 ([M-$C_4H_7O_2$]$^+$, 97%).

C) (S,S)— (+)-N,N-Bis(3,5-di-tert.-butylsalicylidene)-1,2-cyclohexyanediamino-manganese (III) chloride ("Jacobsens Catalyst"; 5 mol %) catalyst and pyridine N-oxide (0.5 eq) were added to a solution of chromene (1 eq.) in dichloromethane at 0° C. A cooled aqueous solution of $NaHPO_4$ (0.05 M) and fresh NaOCl (0.6 M) were added to the mixture. The reaction was allowed to stir at 0° C. for 6 hours. Dichloromethane and Celite® were added to the reaction and filtered through a sinter covered with Celite®. The organic layer of the filtrate was separated from the aqueous layer, washed with brine, dried over $MgSO_4$ and evaporated under reduced pressure. The resulting black oil was re-crystallised in heptane/ethyl acetate (heptane was added first and then ethyl acetate until complete dissolution of the epoxide). ((3S,4R)-2,2-dimethyl-1a,7b-dihydro-2H-1,3-dioxa-cyclopropa[a]napthalen-6-yl)acetic acid isopropyl ester was obtained as white needles.

HPLC-MS (ES+): Rt=1.26 mins 235.26([M-$C_3H_7O$]+, 100%), 277.40 (M+, 40%), 312.51 (13%), 317.49 (15%).

D) ((3S,4R)-2,2-dimethyl-1a,7b-dihydro-2H-1,3-dioxa-cyclopropa[a]napthalen-6-yl)acetic acid isopropyl ester as prepared above was treated with a solution of EtOH:$NH_4OH$ (6:5, v/v) to prepare a 0.2M solution of the epoxide. The solution was heated to 50° C. for 16 hours. On cooling the solvent was removed in vacuo. The crude product obtained could be purified by column chromatography using a gradient elution of ethyl acetate:dichloromethane:MeOH. 7.3 g of pure ((3S,4R)-4-amino-3-hydroxy-2,2-dimethyl-chroman-6-yl)-acetic acid isopropyl ester was obtained.

$^1$H-NMR (δ ppm, $CDCl_3$): 7.28 (s, 1H), 7.05 (dd, 1H, J=1.72, 8.28 Hz), 6.74 (d, 1H, J=8.32 Hz), 5.00 (septet, 1H, J=6.36 Hz), 3.70 (d, 1H, J=9.76 Hz), 3.51 (s, 2H), 3.30 (d, 1H, J=9.52 Hz), 2.90 (broad, s, 3H), 1.47 (s, 3H), 1.23 (d, 6H, J=6.36 Hz), 1.18 (s, 3H).

HPLC-MS (ES+): Rt=1.09 mins 235.29 ([M-$C_3H_7O$]+, 100%), 263.36 (16%), 277.42 ([M-$NH_2$]+, 22%), 294.48 (M+, 38%) ([M+Na]+, 35%).

E) ((3S,4R)-4-Amino-3-hydroxy-2,2-dimethyl-chroman-6-yl)-acetic acid isopropyl ester (54 g) as obtained above was dissolved in dichloromethane (10 volumes) followed by the addition of boc-anhydride (100 g), triethylamine (78 ml) and DMAP (22.5 g). The resulting solution was shaken overnight. The solvent was concentrated in vacuo and the residue purified by column chromatography using heptane:ethylacetate 6:1 to give 66.7 g of product. (3S,4R)-(4-tert.-butoxycarbonylamino-3-hydroxy-2,2-dimethyl-chroman-6-yl)acetic acid isopropyl ester (mono-protected product) and (3S,4R)-(4-tert.-butoxycarbonylamino-3-tert.-butoxycarbonyloxy-2,2-dimethylchroman-6-yl)acetic acid isopropyl ester (di-protected product) were isolated as a 2:1 mixture in favour of the mono-protected product.

$^1$H-NMR (δ ppm, $CDCl_3$): 7.1 (complex, 3H), 6.85 (d, 1H, J=9.04 Hz), 6.75 (d, 0.5H, J=8.32 Hz), 5.0 (complex, 2H), 4.90 (d, 1H, 11.7 Hz), 4.78 (complex, 1H), 3.92 (d, 1H, J=11.7 Hz), 3.50 (s, ), 3.49 (s, ), 1.63 (s, 9H), 1.48 (complex), 1.22 (complex, 12H).

HPLC-MS (ES+): mono-protected Rt=1.71 unassigned; di-protected Rt=1.86 unassigned F) A mixture (66.7 g) of (3S,4R)-(4-tert-butoxycarbonylamino-3-hydroxy-2,2-dimethyl-chroman-6-yl)acetic acid isopropyl ester and (3S,4R)-(4-tert-butoxycarbonylamino-3-tert-butoxycarbonyloxy-2,2-dimethylchroman-6-yl)acetic acid isopropyl ester as obtained above was stirred for 16 hours in a solution of THF:H₂O (1:1, 1.4 liters) and LiOH (14.7 g). The reaction was monitored by HPLC-MS. Then, a further quantity of LiOH (0.26 g) was added and the reaction shaken for a further 4 hours where IPC analysis determined the reaction to be complete. The solution was acidified with 1M HCl dropwise, and extracted with ethyl acetate. The combined organic phases were dried over magnesium sulphate before being concentrated in vacuo to yield as a white solid a mixture (59 g) of (3S,4R)-(4-tert.-butoxycarbonylamino-3-hydroxy-2,2-dimethyl-chroman-6-yl)acetic acid (mono-protected product) and (3S,4R)-(4-tert.-butoxycarbonylamino-3-tert.-butoxycarbonyloxy-2,2-dimethylchroman-6-yl)acetic acid (di-protected product).

HPLC-MS (ES+): mono-protected Rt=1.13 374.19 ([M+Na]+, 70%), 296.07 ([M-C₄H₈]+, 30%), 234.95 ([M-C5H10NO2]+, 55%), 146.82 (100%); di-protected Rt=1.57 925.46 ([2M+Na+H]+, 20%), 474.28 ([M+Na+H]+, 40%), 320.10 (50%), 232.93 (100%).

G) A mixture (4.0 g) of (3S,4R)-(4-tert-butoxycarbonylamino-3-hydroxy-2,2-dimethyl-chroman-6-yl)acetic acid and (3S,4R)-(4-tert-butoxycarbonylamino-3-tert-butoxycarbonyloxy-2,2-dimethylchroman-6-yl)acetic acid as obtained above was dissolved in dichloromethane (50 ml). DIC (1.68 ml), HOBT (1.46 g) and N-benzylpiperazine (1.90 g) was added and the reaction shaken at room temperature for 16 hours. The solution was concentrated in vacuo and the obtained mixture of (3S,4R)-{6-[2-(4-benzylpiperazin-1-yl)-2-oxo-ethyl]-3-hydroxy-2,2-dimethyl-chroman-4-yl}carbamic acid tert-butyl ester (mono-protected product) and (3S,4R)-carbonic acid 6-[2-(4-benzylpiperazin-1-yl)-2-oxoethyl]-4-tert-butoxycarbonylamino-2,2-dimethylchroman-3-yl ester tert.-butyl ester (di-protected product) was purified by column chromatography using a solvent gradient from dichloromethane:ethyl acetate (4:1) to dichloromethane:ethyl acetate (1:1) and then increased to ethyl acetate:MeOH (1:1).

HPLC-MS (ES+): mono-protected Rt=1.12 mins 454.37 ([M-C4H9]+, 100%), 510.41 (M+, 26%), 532.39 ([M+Na]+, 31%); di-protected Rt=1.52 mins 498.34 ([M-C8H18]+, 54%), 554.38 ([M-C4H9]+, 100%), 610.43 (M+, 67%), 632.40 ([M+Na]+, 43%).

H) A mixture (6.0 g) of (3S,4R)-{6-[2-(4-benzylpiperazin-1-yl)-2-oxo-ethyl]-3-hydroxy-2,2-dimethylchroman-4-yl}carbamic acid tert-butyl ester and (3S,4R)-carbonic acid 6-[2-(4-benzylpiperazin-1-yl)-2-oxoethyl]-4-tert-butoxycarbonylamino-2,2-dimethylchroman-3-yl ester tert.-butyl ester as obtained above was dissolved in 4M HCl in dioxane (12.6 ml) and shaken for 16 hours at room temperature. The reaction was monitored by HPLC-MS and more reagent was added as required to complete the reaction. On completion of the reaction the solution was concentrated in vacuo and the residue re-dissolved in dichloromethane:MeOH (1:1). AMPS (2.5 eq) was added the suspension shaken at room temperature for 5 hours. The solution was filtered and concentrated in vacuo to yield (3S,4R)-2-(4-amino-3-hydroxy-2,2-dimethylchroman-6-yl)-1-(4-benzylpiperazine-1-yl)ethanone, which was used without further purification.

HPLC-MS (ES+):Rt=0.65 mins, 819.43 ([2M+H]+, 20%), 410.28 ([M+H]+, 50%), 393.25 ([M-NH2]+, 100%).

I) (3S,4R)-2-(4-amino-3-hydroxy-2,2-dimethylchroman-6-yl)-1-(4-benzylpiperazine-1-yl)ethanone as obtained above (15 mg) was dissolved in dichloromethane (0.6 ml). PS-piperidine (20 mg) was added, followed by 4-propylbenzenesulfonyl chloride (1 eq). The reaction was shaken at room temperature for 2 days. The resin was filtered and PS-AMPS (30 mg) was added, in addition to more dichloromethane as required. The reaction was shaken at room temperature for a further 16 hours before being filtered and concentrated in vacuo to yield the title compound.
HPLC-MS (ES+): 592.27 ([M+H]+, 100%)

EXAMPLE 2

(3S,4R)-2-{4-[(4-Chloro-3-methylbenzenesulfonyl)-(2-ethylbutylamino]-3-hydroxy-2,2-dimethylchroman-6-yl}-N-[2-(1-methylpyrrolidin-2-yl)ethyl]acetamide

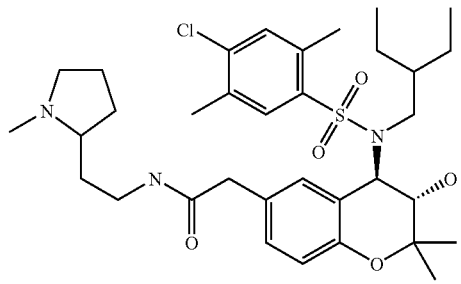

A) A mixture (4.0 g) of (3S,4R)-(4-tert-butoxycarbonylamino-3-hydroxy-2,2-dimethyl-chroman-6-yl)acetic acid and (3S,4R)-(4-tert-butoxycarbonylamino-3-tert-butoxycarbonyloxy-2,2-dimethylchroman-6-yl)acetic acid (for preparation see example 1F) above) was dissolved in dichloromethane (50 ml). DIC (1.68 ml), HOBT (1.46 g) and 2-(2-aminoethyl)-1-methylpyrrolidine (1.37 g) was added and the reaction shaken at room temperature for 16 hours. The solution was concentrated in vacuo and the obtained mixture of (3S,4R)-(3-hydroxy-2,2-dimethyl-6-{[2-(1-methylpyrrolidin-2-yl)ethylcarbamoyl]methyl}chroman-4-yl)carbamic acid tert.-butyl ester (mono-protected product) and (3S,4R)-carbonic acid 4-tert.-butoxycarbonylamino-2,2-dimethyl-6-{[2-(1-methylpyrrolidin-2-yl)ethylcarbamoyl]methyl}chroman-3-yl ester tert.--butyl ester (di-protected product) purified by column chromatography using a solvent gradient from dichloromethane:ethyl acetate (4:1) to dichloromethane:ethyl acetate (1:1) and then increased to ethyl acetate:MeOH (1:1).

HPLC-MS (ES+): mono-protected Rt=1.05 mins 462.51 (M+, 100%); di-protected Rt=1.46 mins 562.47 (M+, 100%).

B) A mixture (6.0 g) of (3S,4R)-(3-hydroxy-2,2-dimethyl-6-{[2-(1-methylpyrrolidin-2-yl)ethylcarbamoyl]methyl}chroman-4-yl)carbamic acid tert-butyl ester and (3S,4R)-carbonic acid 4-tert-butoxycarbonylamino-2,2-dimethyl-6-{[2-(1-methylpyrrolidin-2-yl)ethyl-carbamoyl]methyl}chroman-3-yl ester tert-butyl ester as obtained above was dissolved in 4M HCl in dioxane (12.6 ml) and shaken for 16 hours at room temperature. The reaction was monitored by HPLC-MS and more reagent was added as required to complete the reaction. On completion of the reaction the solution was concentrated in vacuo and the residue re-dissolved in dichloromethane:MeOH (1:1). AMPS (2.5 eq) was added and the suspension was shaken at room temperature for 5 hours. The solution was filtered and concentrated in vacuo to yield (3S,4R)-2-(4-amino-3-hydroxy-2,2-dimethylchroman-6-yl)-N-[2-(1-methylpyrrolidin-2-yl)ethyl]-acetamide, which was used without further purification.

HPLC-MS (ES+): Rt=0.72 mins 345.49([M-NH2]+, 84%), 362.53 (M+, 100%), 384.53 ([M+Na]+, 15%)

C) (3S,4R)-2-(4-amino-3-hydroxy-2,2-dimethylchroman-6-yl)-N-[2-(1-methylpyrrolidin-2-yl)ethyl]acetamide as obtained above was dissolved in methanol (20 ml) and TMOF (0.22 ml) added followed by molecular sieves. 2-Ethylbutyraldehyde was added and the reaction shaken at room temperature for 16 hours. On completion of imine formation, confirmed by HPLC-MS and/or $^1$H NMR analysis, PS—BH$_4$ (5 eq) was added and the reaction shaken for an additional 16 hours. Further PS—BH$_4$ was added as required to reach completion of the reaction. The crude secondary amine was dissolved in dichloromethane and PS—CHO (0.4 eq) and AMPS (0.6 eq) were added sequentially. The reaction mixture was shaken at room temperature for a further 16 hours. The resin was then filtered, washed with THF and the filtrates were combined and concentrated in vacuo. The crude product was purified by column chromatography using a gradient of dichloromethane to dichloromethane:MeOH (20:80) to yield (3S,4R)-2-[4-(2-ethylbutylamino)-3-hydroxy-2,2-dimethylchroman-6-yl]-N-[2-(1-methylpyrrolidin-2-yl)ethyl]acetamide.

D) (3S,4R)-2-[4-(2-ethylbutylamino)-3-hydroxy-2,2-dimethylchroman-6-yl]-N-[2-(1-methylpyrrolidin-2-yl)ethyl]acetamide as obtained above (15 mg) was dissolved in dichloromethane (0.6 ml). PS-Piperidine (20 mg) was added followed by a solution of 4-chloro-2,5-dimethylbenzenesulfonyl chloride (3 eq) in dichloromethane (0.4 ml). The reaction was shaken at room temperature for 2 days. The resin was filtered and PS-AMPS (30 mg) was added, in addition to more dichloromethane if required. The reaction was shaken at room temperature for a further 16 hours before being filtered and concentrated in vacuo to yield the title compound.

HPLC-MS (ES+): 648.53/650.53 ([M+H]+, 100%)

EXAMPLE 3

(3S,4R)-2-{3-Hydroxy-4-[(4-iodobenzenesulfonyl)-(3-methylbutyl)amino]-2,2-dimethylchroman-6-yl}-N-(2-piperidin-1-ylethyl)acetamide

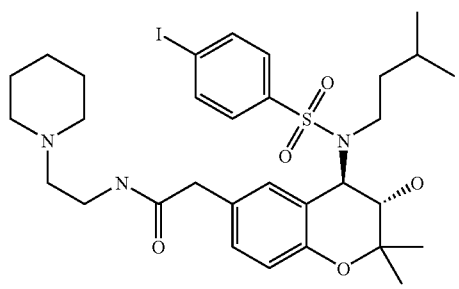

A) A mixture (4.0 g) of (3S,4R)-(4-tert-butoxycarbonylamino-3-hydroxy-2,2-dimethyl-chroman-6-yl)acetic acid and (3S,4R)-(4-tert-butoxycarbonylamino-3-tert-butoxycarbonyloxy-2,2-dimethylchroman-6-yl)acetic acid (for preparation see example 1F) above) was dissolved in dichloromethane (50 ml). DIC (1.68 ml), HOBT (1.46 g) and N-(2-aminoethyl)piperidine (1.37 g) was added and the reaction shaken at room temperature for 16 hours. The solution was concentrated in vacuo and the crude products purified by column chromatography using a solvent gradient from dichloromethane:ethyl acetate (4:1) to dichloromethane:ethyl acetate (1:1) to eliminate the reagents and side-products and then increased to ethyl acetate:MeOH (1:1) to elute a mixture of (3S,4R)-{3-hydroxy-2,2-dimethyl-6-[(2-piperidin-1-ylethyl-carbamoyl)methyl]chroman-4-yl)carbamic acid tert.-butyl ester (mono-protected product) and (3S,4R)-carbonic acid 4-tert.-butoxycarbonylamino-2,2-dimethyl-6-[(2-piperidin-1-ylethylcarbamoyl)-methyl]chroman-3-yl ester tert.-butyl ester (di-protected product).

HPLC-MS (ES+): mono-protected Rt=1.03 mins 406.40 ([M-C4H9]+, 30%), 462.49 (M+, 100%), 484.46 ([M+Na]+, 14%); di-protected Rt=1.44 mins 506.46 ([M-C$_4$H$_9$]+, 14%), 562.50 (M+, 100%), 584.47 ([M+Na]+, 15%).

B) A mixture (6.0 g) of (3S,4R)-{3-hydroxy-2,2-dimethyl-6-[(2-piperidin-1-ylethylcarbamoyl)methyl]chroman-4-yl) carbamic acid tert-butyl ester and (3S,4R)-carbonic acid 4-tert.-butoxycarbonylamino-2,2-dimethyl-6-[(2-piperidin-1-ylethylcarbamoyl)methyl]chroman-3-yl ester tert-butyl ester as obtained above was dissolved in 4M HCl in dioxane (12.6 ml) and shaken for 16 hours at room temperature. The reaction was monitored by HPLC-MS and more reagent was added as required to complete the reaction. On completion of the reaction the solution was concentrated in vacuo and the residue re-dissolved in dichloromethane:MeOH (1:1). AMPS (2.5 eq) was added and the suspension was shaken at room temperature for 5 hours. The solution was filtered and concentrated in vacuo to yield (3S,4R)-2-(4-amino-3-hydroxy-2,2-dimethylchroman-6-yl)-N-(2-piperidin-1-ylethyl)cetamide, which was used without further purification.

HPLC-MS (ES+): Rt=0.75 mins 361.57([M-NH2]+, 41%), 378.61 (M+, 100%)

C) (3S,4R)-2-(4-amino-3-hydroxy-2,2-dimethylchroman-6-yl)-N-(2-piperidin-1-ylethyl)acetamide (1 eq, 2 mmol) as obtained above was dissolved in methanol (20 ml) and TMOF (0.22 ml) added followed by molecular sieves. Isovaleraldehyde was added and the reaction shaken at room temperature for 16 hours. On completion of imine formation, confirmed by HPLC-MS and $^1$H-NMR analysis PS—BH$_4$ (5 eq) was added and the reaction shaken for an additional 16 hours. Further PS—BH$_4$ was added as required to complete the reaction. The crude secondary amine was dissolved in dichloromethane and PS—CHO (0.4 eq) and AMPS (0.6 eq) were added sequentially. The reaction mixture was shaken at room temperature for a further 16 hours. The resin was then filtered, washed with THF and the filtrates combined and concentrated in vacuo. The residue was purified by column chromatography using a gradient of dichloromethane to dichloromethane:MeOH (20:80) to yield (3S,4R)-2-[3-hydroxy-2,2-dimethyl-4-(3-methylbutylamino)chroman-6-yl]-N-(2-piperidin-1-ylethyl)acetamide.

D) (3S,4R)-2-[3-hydroxy-2,2-dimethyl-4-(3-methylbutylamino)chroman-6-yl]-N-(2-piperidin-1-ylethyl)acetamide (15 mg) as obtained above was dissolved in dichloromethane (0.6 ml). PS-Piperidine (20 mg) was added followed by a solution of 4-iodobenzenesulfonyl chloride (3 eq) in dichloromethane (0.4 ml). The reaction was shaken at room temperature for 2 days. The resin was filtered and PS-AMPS (30 mg) was added, in addition to more dichloromethane if required. The reaction was shaken at room temperature for a further 16 hours before being filtered and concentrated in vacuo to yield of the title compound.

EXAMPLE 4

(3S,4R)—N-(1-Benzylpyrrolidin-3R-yl)-2-{4-[(2-ethylbutyl)-(3-methoxybenzenesulfonyl)amino]-3-hydroxy-2,2-dimethylchroman-6-yl}acetamide

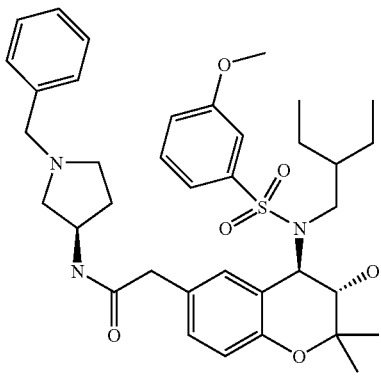

A) A mixture (4.0 g) of (3S,4R)-(4-tert-butoxycarbonylamino-3-hydroxy-2,2-dimethyl-chroman-6-yl)acetic acid and (3S,4R)-(4-tert-butoxycarbonylamino-3-tert-butoxycarbonyloxy-2,2-dimethylchroman-6-yl)acetic acid was dissolved in dichloromethane (50 ml). DIC (1.68 ml), HOBT (1.46 g) and (3R)-(−)-1-benzyl-3-aminopyrrolidine (1.89 g) was added and the reaction shaken at room temperature for 16 hours. The solution was concentrated in vacuo and the crude products purified by column chromatography using a solvent gradient from dichloromethane:ethyl acetate (4:1) to dichloromethane:ethyl acetate (1:1) and then increased to ethyl acetate:MeOH (1:1) to elute a mixture of (3S,4R)-{6-[(1-benzylpyrrolidin-3R-ylcarbamoyl)methyl]-3-hydroxy-2,2-dimethylchroman-4-yl}carbamic acid tert.-butyl ester (mono-protected product) and (3S,4R)-carbonic acid 6-[(1-benzylpyrrolidin-3R-ylcarbamoyl)methyl]-4-tert.-butoxycarbonylamino-2,2-dimethylchroman-3-yl ester tert.-butyl ester (di-protected product).

HPLC-MS (ES+): mono-protected Rt=1.13 mins 454.45 ([M-C4H9]+, 63%), 510.51 (M+, 100%), 532.49 ([M+Na]+, 46%); di-protected Rt=1.52 mins 554.49 ([M-C4H9]+, 32%), 610.54 (M+, 100%), 632.50 ([M+Na]+, 16%).

B) A mixture (6.0 g) of (3S,4R)-{6-[(1-benzylpyrrolidin-3R-ylcarbamoyl)methyl]-3-hydroxy-2,2-dimethylchroman-4-yl}carbamic acid tert-butyl ester and (3S,4R)-carbonic acid 6-[(1-benzylpyrrolidin-3R-ylcarbamoyl)methyl]-4-tert-butoxycarbonylamino-2,2-dimethylchroman-3-yl ester tert-butyl ester as obtained above was dissolved in 4M HCl in dioxane (12.6 ml) and shaken for 16 hours at room temperature. The reaction was monitored by HPLC-MS and more reagent was added as required to complete the reaction. On completion of the reaction the solution was concentrated in vacuo and the residue re-dissolved in dichloromethane:MeOH (1:1). AMPS (2.5 eq) was added the suspension shaken at room temperature for 5 hours. The solution was filtered and concentrated in vacuo to yield (3S,4R)-2-(4-amino-3-hydroxy-2,2-dimethylchroman-6-yl)-N-1-benzylpyrrolidin-3R-yl)acetamide, which was used without further purification.

HPLC-MS (ES+): Rt=0.67 mins 361.56([M-OH]+, 100%), 378.59 (M+, 72%), 400.60 ([M+Na]+, 35%).

C) (3S,4R)-2-(4-amino-3-hydroxy-2,2-dimethylchroman-6-yl)-N-1-benzylpyrrolidin-3R-yl)acetamide was dissolved in methanol (20 ml) and TMOF (0.22 ml) added followed by molecular sieves. 2-Ethylbutyraldehyde was added and the reaction shaken at room temperature for 16 hours. On completion of imine formation, confirmed by HPLC-MS and $^1$H-NMR analysis, PS—BH$_4$ (5 eq) was added and the reaction shaken for an additional 16 hours. Further PS—BH$_4$ was added as required to complete the reaction. The crude secondary amine was dissolved in dichloromethane and PS—CHO (0.4 eq) and AMPS (0.6 eq) were added sequentially. The reaction mixture was shaken at room temperature for a further 16 hours. The resin was then filtered, washed with THF and the filtrates combined and concentrated in vacuo. The residue was purified by column chromatography using a gradient of dichloromethane:MeOH (20:80) to yield (3S,4R)—N-(1-benzylpyrrolidin-3R-yl)-2-[4-(2-ethylbutylamino)-3-hydroxy-2,2-dimethylchroman-6-yl]acetamide.

D) (3S,4R)—N-(1-benzylpyrrolidin-3-yl)-2-[4-(2-ethylbutylamino)-3-hydroxy-2,2-dimethylchroman-6-yl]acetamide (15 mg) as obtained above was dissolved in dichloromethane (0.6 ml). PS-Piperidine (20 mg) was added followed by a solution of 4-iodobenzenesulfonyl chloride (3 eq) in dichloromethane (0.4 ml). The reaction was shaken at room temperature for 2 days. The resin was filtered and PS-AMPS (30 mg) was added, in addition to more dichloromethane as required. The reaction was shaken at room temperature for a further 16 hours before being filtered and concentrated in vacuo to yield the title compound.

HPLC-MS (ES+): 664.73 ([M+H]+, 100%)

EXAMPLE 5

(3S,4R)—N-[2-(Butylethylamino)ethyl]-2-{4-[(2-ethylbutyl)-(4-iodobenzenesulfonyl)amino]-3-hydroxy-2,2-dimethylchroman-6-yl)acetamide

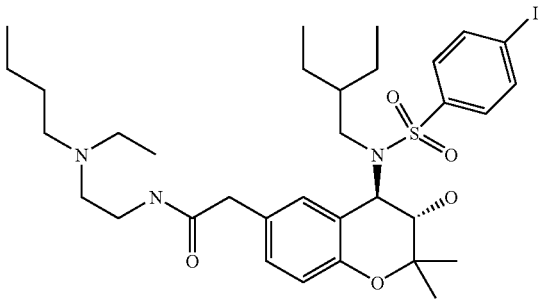

A) A mixture (4.0 g) of (3S,4R)-(4-tert-butoxycarbonylamino-3-hydroxy-2,2-dimethyl-chroman-6-yl)acetic acid and (3S,4R)-(4-tert-butoxycarbonylamino-3-tert-butoxycarbonyloxy-2,2-dimethylchroman-6-yl)acetic acid (for preparation see example 1F) above) was dissolved in dichloromethane (50 ml). DIC (1.68 ml), HOBT (1.46 g) and 2-(ethyl-N-butylamino)ethylamine (1.55 g) was added and the reaction shaken at room temperature for 16 hours.

The solution was concentrated in vacuo and the residue purified by column chromatography using a solvent gradient from dichloromethane:ethyl acetate (4:1) to dichloromethane:ethyl acetate (1:1) and then increased to ethyl acetate:MeOH (1:1) to elute a mixture of (3S,4R)-(6-{[2-(butylethylamino)ethylcarbornyl]methy}-3-hydroxy-2,2-dimethylchroman-4-yl)carbamic acid tert.-butyl ester (mono-protected product) and (3S,4R)-carbonic acid 4-tert.-butoxycarbonylamino-6-{[2-(butylethylamino)ethyl-carbamoyl]methyl}-2,2-dimethylchroman-3-yl ester tert.-butyl ester (di-protected product).

HPLC-MS (ES+): mono-protected Rt=1.12 mins 478.58 (M+, 100%); di-protected Rt=1.53 mins 578.56 (M+, 100%).

B) A mixture (6.0 g) of (3S,4R)-(6-{[2-(butylethylamino)ethylcarbornyl]methy}-3-hydroxy-2,2-dimethylchroman-4-yl)carbamic acid tert-butyl ester and (3S,4R)-carbonic acid 4-tert-butoxycarbonylamino-6-{[2-(butylethylamino)ethylcarbamoyl]methyl}-2,2-dimethylchroman-3-yl ester tert-butyl ester as obtained above was dissolved in 4M HCl in dioxane (12.6 ml) and shaken for 16 hours at room temperature. The reaction was monitored by HPLC-MS and more reagent was added as required to complete the reaction. On completion of the reaction the solution was concentrated in vacuo and the residue re-dissolved in dichloromethane:MeOH (1:1). AMPS (2.5 eq) was added and the suspension shaken at room temperature for 5 hours. The solution was filtered and concentrated in vacuo to yield (3S,4R)-2-(4-amino-3-hydroxy-2,2-dimethylchroman-6-yl)-N-[2-(butylethylamino)ethyl]acetamide, which was used without further purification.

HPLC-MS (ES+): Rt=0.84 mins 407.43([M-OH]+, 100%), 424.47 (M+, 44%)

C) (3S,4R)-2-(4-amino-3-hydroxy-2,2-dimethylchroman-6-yl)-N-[2-(butylethylamino)ethyl]acetamide as obtained above was dissolved in methanol (20 ml) and TMOF (0.22 ml) added followed by molecular sieves. 2-Ethylbutyraldehyde was added and the reaction shaken at room temperature for 16 hours. On completion of imine formation, confirmed by HPLC-MS and ¹H-NMR analysis, PS—BH₄ (5 eq) was added and the reaction was shaken for an additional 16 hours. Further PS—BH₄ was added as required to complete the reaction. The crude secondary amine was dissolved in dichloromethane and PS—CHO (0.4 eq) and AMPS (0.6 eq) were added sequentially. The reaction mixture was shaken at room temperature for a further 16 hours. The resin was then filtered, washed with THF and the filtrates combined and concentrated in vacuo. The residue was purified by column chromatography using a gradient of dichloromethane to dichloromethane:MeOH (20:80) to yield (3S,4R)—N-[2-(butylethylamino)-ethyl]-2-[4-(2-ethylbutylamino)-3-hydroxy-2,2-dimethylchroman-6-yl]acetamide.

D) (3S,4R)—N-[2-(butylethylamino)-ethyl]-2-[4-(2-ethylbutylamino)-3-hydroxy-2,2-dimethylchroman-6-yl]acetamide (15 mg) as obtained above was dissolved in dichloromethane (0.6 ml). PS-Piperidine (20 mg) was added followed by a solution of 4-iodobenzenesulfonyl chloride (3 eq) in dichloromethane (0.4 ml). The reaction was shaken at room temperature for 2 days. The resin was filtered and PS-AMPS (30 mg) was added, in addition to more dichloromethane as required. The reaction was shaken at room temperature for a further 16 hours before being filtered and concentrated in vacuo to yield the title compound.

HPLC-MS (ES+): 728.68 ([M+H]+, 100%).

EXAMPLE 6

(3S,4R)—N-(4-Benzylmorpholin-2-ylmethyl)-2-{4-[(3-methoxybenzenesulfonyl)-3-methylbutyl)amino]-3-hydroxy-2,2-dimethylchroman-6-yl}acetamide

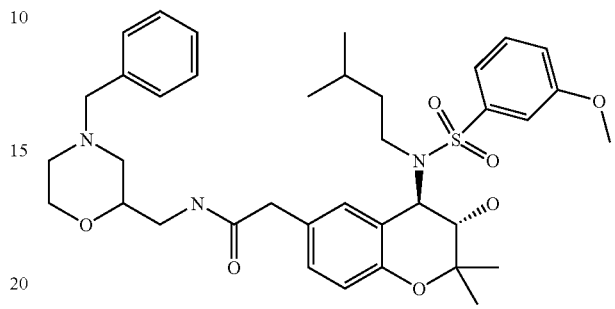

A) A mixture (4.0 g) of (3S,4R)-(4-tert-butoxycarbonylamino-3-hydroxy-2,2-dimethyl-chroman-6-yl)acetic acid and (3S,4R)-(4-tert-butoxycarbonylamino-3-tert-butoxycarbonyloxy-2,2-dimethylchroman-6-yl)acetic acid (for preparation see example 1F) above) was dissolved in dichloromethane (50 ml). DIC (1.68 ml), HOBT (1.46 g) and N-benzyl-3-aminomethylmorpholine (2.21 g) was added and the reaction shaken at room temperature for 16 hours. The solution was concentrated in vacuo and the residue purified by column chromatography using a solvent gradient from dichloromethane:ethyl acetate (4:1) to dichloromethane:ethyl acetate (1:1) and then increased to ethyl acetate:MeOH (1:1) to elute of a mixture of (3S,4R)-(6-{[(4-benzylmorpholin-2-ylmethyl)carbamoyl]methyl}-3-hydroxy-2,2-dimethyl-chroman-4-yl)carbamic acid tert.-butylester (mono-protected product) and (3S,4R)-carbonic acid 6-{[(4-benzylmorpholin-2-ylmethyl)carbamoyl]methyl}-4-tert.-butoxycarbonylamino-2,2-dimethyl-chroman-3-yl ester tert.-butyl ester (di-protected product).

HPLC-MS (ES+): mono-protected Rt=1.15 mins 484.38 ([M-C4H9]+, 17%), 540.37 (M+, 100%), 562.34 ([M+Na]+, 12%); di-protected Rt=1.51 mins 584.33 ([M-C4H9]+, 8%), 640.43 (M+, 100%), 662.40 ([M+Na]+, 10%).

B) A mixture (6.0 g) of (3S,4R)-(6-{[(4-benzylmorpholin-2-ylmethyl)carbamoyl]methyl}-3-hydroxy-2,2-dimethyl-chroman-4-yl)carbamic acid tert-butylester and (3S,4R)-carbonic acid 6-{[(4-benzyl morpholin-2-ylmethyl)carbamoyl]methyl}-4-tert-butoxycarbonylamino-2,2-dimethyl chroman-3-yl ester tert-butyl ester as obtained above was dissolved in 4M HCl in dioxane (12.6 ml) and shaken for 16 hours at room temperature. The reaction was monitored by HPLC-MS and more reagent was added as required to complete the reaction. On completion of the reaction the solution was concentrated in vacuo and the residue re-dissolved in dichloromethane:MeOH (1:1). AMPS (2.5 eq) was added the suspension shaken at room temperature for 5 hours. The solution was filtered and concentrated in vacuo to yield (3S,4R)-2-(4-amino-3-hydroxy-2,2-dimethylchroman-6-yl)-N-(4-benzylmorpholin-2-ylmethyl)acetamide, which was used without further purification.

HPLC-MS (ES+): Rt=0.84 mins 423.59([M-OH]+, 100%), 440.62 (M+, 18%), 462.61 ([M+Na]+, 16%).

C) (3S,4R)-2-(4-amino-3-hydroxy-2,2-dimethylchroman-6-yl)-N-(4-benzylmorpholin-2-ylmethyl)acetamide (1 eq, 2 mmol) as obtained above was dissolved in methanol (20 ml) and Tmof (0.22 ml) added followed by molecular sieves. Isovaleraldehyde (1.0 eq, 2 mmol) was added and the reaction shaken at room temperature for 16 hours. On completion of imine formation, confirmed by HPLC-MS and/or 1H nmr analysis PS—BH$_4$ (5 eq) was added and the reaction shaken for an additional 16 hours. Further PS—BH$_4$ can be added as required if the reaction fails to reach completion. The crude secondary amine was dissolved in dichloromethane and PS—CHO (0.4 eq) and AMPS (0.6 eq) were added sequentially. The reaction mixture was shaken at room temperature for a further 16 hours. The resin was then filtered, washed with THF and the filtrates combined and concentrated in vacuo. The residue was purified by column chromatography using a gradient of dichloromethane to dichloromethane:MeOH (20:80) to yield (3S,4R)—N-(4-benzylmorpholin-2-ylmethyl)-2-[4-(3-methylbutylamino)-3-hydroxy-2,2-dimethylchroman-6-yl]acetamide.

D) (3S,4R)—N-(4-benzylmorpholin-2-ylmethyl)-2-[4-(3-methylbutylamino)-3-hydroxy-2,2-dimethylchroman-6-yl]acetamide (15 mg) as obtained above was dissolved in dichloromethane (0.6 ml). PS-Piperidine (20 mg) was added followed by a solution of 3-methoxybenzenesulfonyl chloride (3 eq) in dichloromethane (0.4 ml). The reaction was shaken at room temperature for 2 days. The resin was filtered and PS-AMPS (30 mg) was added, in addition to more dichloromethane as required. The reaction was shaken at room temperature for a further 16 hours before being filtered and concentrated in vacuo to yield the title compound.

HPLC-MS (ES+): 702.56 ([M+Na]+, 21%), 680.57 ([M+H]+, 100%), 256.27 ([M-C25H31N2O4]+, 40%).

EXAMPLE 7

(3S,4R)—N-{6-[2-(4-benzylpiperazin-1-yl)-2-oxoethyl]-3-hydroxy-2,2-dimethylchroman-4-yl}-N-cyclopropylmethyl-4-methylbenzenesulfonamide

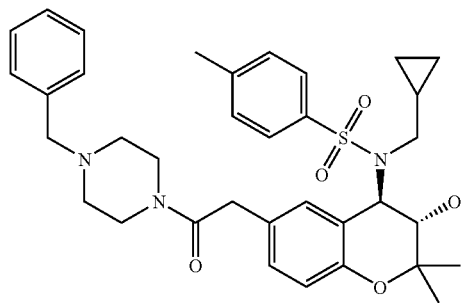

A) (3S,4R)-2-(4-amino-3-hydroxy-2,2-dimethylchroman-6-yl)-1-(4-benzylpiperazine-1-yl)ethanone (for preparation see example 1H) above) was dissolved in methanol (20 ml) and TMOF (0.22 ml) added followed by molecular sieves. Cyclopropanecarboxaldehyde was added and the reaction shaken at room temperature for 16 hours. On completion of imine formation, confirmed by HPLC-MS and $^1$H-NMR analysis, PS—BH$_4$ (5 eq) was added and the reaction shaken for an additional 16 hours. Further PS—BH$_4$ was added as required to complete the reaction. The crude secondary amine was dissolved in dichloromethane and PS—CHO (0.4 eq) and AMPS (0.6 eq) were added sequentially. The reaction mixture was shaken at room temperature for a further 16 hours. The resin was then filtered, washed with THF and the filtrates combined and concentrated in vacuo. The residue was purified by column chromatography using a gradient of dichloromethane to dichloromethane:MeOH (20:80) to yield (3S,4R)-1-(4-benzylpiperazin-1-yl)-2-[4-(cyclopropylmethylamino)-3-hydroxy-2,2-dimethylchroman-6-yl]ethanone.

B) (3S,4R)-1-(4-benzylpiperazin-1-yl)-2-[4-(cyclopropylmethylamino)-3-hydroxy-2,2-dimethylchroman-6-yl]ethanone as obtained above (15 mg) was dissolved in dichloromethane (0.6 ml). PS-Piperidine (20 mg) was added followed by a solution of 4-methylbenzenesulfonyl chloride (3 eq) in dichloromethane (0.4 ml). The reaction was shaken at room temperature for 2 days. The resin was filtered and PS-AMPS (30 mg) was added, in addition to more dichloromethane as required. The reaction was shaken at room temperature for a further 16 hours before being filtered and concentrated in vacuo to yield of the title compound.

HPLC-MS (ES+): 618.65 ([M+H]+, 100%).

EXAMPLE 8

4-Ethyl-N-((3S,4R)-3-hydroxy-2,2-dimethyl-6-{2-oxo-2-[4-(pyridin-3-ylmethyl)piperazin-1-yl]ethyl}-3,4-dihydro-2H-chromen-4-yl)benzenesulfonamide

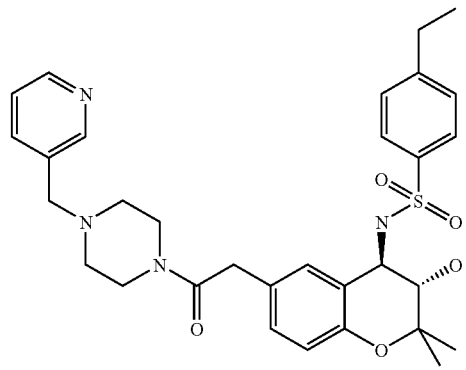

A) Methyl-4-hydroxyphenylacetate (25.0 g), 3,3-dimethylacrolein (14.5 ml) and phenylboronic acid (18.3 g) were refluxed for 7 hours in 1.01 of anhydrous toluene. Glacial acetic acid (60 ml) was then added and the resulting mixture was heated under reflux for another 7 hours while progress was monitored by thin layer chromatography (=TLC). The mixture was then cooled, largely evaporated in vacuo and the residue was poured into a 1:1 mixture of 300 ml ethyl acetate/water. The pH was adjusted to 5 with sodium carbonate and the ethyl acetate layer was separated and concentrated in vacuo. Column chromatography of the residue (mobile phase: petroleum ether/ethyl acetate 10:1) yielded 16 g methyl (2,2-dimethyl-2H-chromen-6-yl)acetate as a pale-yellow oil.

B) Methyl (2,2-dimethyl-2H-chromen-6-yl)acetate (18.3 g) was suspended in 125 ml of ethyl alcohol. 150 ml of a 15% sodium hydroxide solution were added and the mixture was stirred 30 min. at room temperature. Subsequently, 300 ml of water and 150 ml of ethyl acetate were added and the resulting mixture was stirred vigorously for 10 min.

The organic layer was separated and discarded. The alkaline aqueous layer was washed once with 100 ml of ethyl acetate. The layers were separated and the aqueous layer was acidified to pH 2,0 with aqueous hydrochloric acid. 200 ml of ethyl acetate were then added and the resulting mixture was stirred vigorously for 10 min. The organic layer was separated, dried over Na2SO4, filtered off and concentrated in vacuo. The yellow residue was cooled and then charged with petroleum ether and stirred for 30 minutes. The resulting crystals were filtered off and dried in vacuo at 50° C. to yield 6.2 g of (2,2-dimethyl-2H-chromen-6-yl)acetic acid. The mother liquor was concentrated in vacuo and after cooling charged again with petroleum ether. The obtained crystals were dried in vacuo to yield another 2.9 g of (2,2-dimethyl-2H-chromen-6-yl)acetic acid.

C) (2,2-Dimethyl-2H-chromen-6-yl)acetic acid as obtained above (31 g, combined yields from several batches) was dissolved in dichloromethane (450 ml) and cc. $H_2SO_4$ (1.5 ml) was added. To this receiving solution, 2-Methylpropen (21.0 g) was added at −10° C. and the reaction mixture was subsequently stirred for 6 hours at room temperature. Then, water (500 ml) was added and the mixture allowed to stir for 10 minutes. The organic layer was extracted with aqueous $NaHCO_3$-solution, washed with brine, dried over $Na_2SO_4$, filtered and evaporated. Drying of the residue in vacuo yielded tert.-butyl(2,2-dimethyl-2H-chromen-6-yl)acetate (30 g) as a brown oil.

D) Tert.-butyl(2,2-dimethyl-2H-chromen-6-yl)acetate as obtained above (30.0 g) was dissolved in dichloromethane (600 ml) and (S,S)-(+)-N,N'-Bis-(3,5-di-tert.-butylsalicyliden)-1,2-cyclohexan-diamino-mangan (III)-chloride (4.25 g) and pyridine-N-oxide (5.25 g) were added. A commercially available aqueous NaOCl-solution (555 ml; acquired from Fluka; assay 10% at room temperature) and a 9% aqueous $Na_2HPO_4$-solution (75 ml) were added under ice cooling over a period of 45 minutes. The resulting mixture was then stirred for 4 hours at 0° C. The organic layer was filtered off (type 503 Celite®), washed with dichloromethane and the combined organic layers were dried over $Na_2SO_4$. Filtration and evaporation in vacuo yielded a brown oil which was dissolved in diethyl ether. Ligroin was added until crystallisation started. The crystals were filtered by suction filtration and dried to yield tert.-butyl-[(1aS,7bS)-2,2-dimethyl-1a,7b-dihydro-2H-oxireno[c]chromen-6-yl]acetate (18.4 g).

E) Tert.-butyl [(1aS,7bS)-2,2-dimethyl-1a,7b-dihydro-2H-oxireno[c]chromen-6-yl]acetate as obtained above (18.4 g) was dissolved in ethanol (300 ml). Concentrated $NH_4OH$ (300 ml) was added to this receiving solution, and the resulting mixture was stirred for one hour and then kept over night at room temperature. Dichloromethane (400 ml) was added and stirring was continued for another 15 minutes. The organic layer was dried over $Na_2SO_4$, filtered and largely evaporated in vacuo to give a crude oil. The oil was dissolved in diethyl ether, extracted with water and the organic layer was dried over $Na_2SO_4$. Filtration, evaporation and drying yielded tert.-butyl [(3S,4R)-4-amino-3-hydroxy-2,2-dimethyl-3,4-dihydro-2H-chromen-6-yl]acetate (16.3 g) as a brown oil.

F) To a solution of tert.-butyl [(3S,4R)-4-amino-3-hydroxy-2,2-dimethyl-3,4-dihydro-2H-chromen-6-yl]acetate as obtained above (12.0 g) in dichloromethane (280 ml) was first added triethylamine (10.8 ml) and then 4-ethylsulfonylchloride (80 g). The resulting suspension was stirred for 5 hours at room temperature before it was extracted with water. The organic layer was washed with an aqueous $NaHCO_3$-solution, dried over $Na_2SO_4$, filtered and finally evaporated in vacuo to yield tert.-butyl ((3S,4R)-4-{[(4-ethylphenyl)sulfonyl]amino}-3-hydroxy-2,2-dimethyl-3,4-dihydro-2H-chromen-6-yl)acetate (19.6 g) as a brown oil. For further purification, 1.8 g of the oily product was chromatographed (medium pressure liquid chromatography, MPLC; stationary phase Sili Tech® (32-63, 60 A), mobile phase cyclohexane/ethyl acetate 3:1).

G) To a solution of tert.-butyl ((3S,4R)-4-{[(4-ethylphenyl)sulfonyl]amino}-3-hydroxy-2,2-dimethyl-3,4-dihydro-2H-chromen-6-yl)acetate as obtained above (17.2 g) in toluene (170 ml) trifluoroacetic acid (17 ml) was added. The reaction mixture was stirred for 5.5 hours at 40° C. before it was extracted with water (200 ml). The organic layer was extracted with an aqueous $Na_2CO_3$-solution. The aqueous layer was adjusted to pH 6 (HCl) and subsequently extracted twice with ethyl acetate. The combined organic layers were dried over $Na_2SO_4$, filtered and evaporated in vacuo to yield a crude brown oil. The oil was dissolved in diethyl ether and ligroin was added. The mixture was allowed to stir at room temperature until completion of crystallisation. The obtained crystals were sucked off and dried to yield ((3S,4R)-4-{[(4-ethylphenyl)sulfonyl]amino}-3-hydroxy-2,2-dimethyl-3,4-dihydro-2H-chromen-6-yl)acetic acid (9.3 g).

H) To a solution of 1.3 g ((3S,4R)-4-{[(4-ethylphenyl)sulfonyl]amino}-3-hydroxy-2,2-dimethyl-3,4-dihydro-2H-chromen-6-yl)acetic acid in 45 ml THF in a 250 ml round-bottomed flask was added 550 mg CDI. The suspension was stirred at room temperature for 0.5 hours. 600 mg 3-pyridylmethylpiperazine was added and stirred for 4 hours. Afterwards, the mixture was kept overnight at room temperature. The next day, the mixture was evaporated to dryness and dissolved in 2:1 ethyl acetate/$H_2O$. The solution was extracted with aqueous sodium hydroxide pH 10 and afterwards with aqueous HCl pH1. The pH of the HCl layer was adjusted to pH 8 with aqueous NaOH and extracted with ethyl acetate. The organic layer was dried over $Na_2SO_4$, filtered and evaporated in vacuo to give 0.85 g of a yellow foam. The foam was dissolved in isopropanol and three drops MeOH were added. 6N HCl dissolved in isopropanol was added and crystallisation of the hydrochloride started immediately. The crystals were sucked off, washed with diethyl ether and dried to give 0.75 g 4-ethyl-N-((3S,4R)-3-hydroxy-2,2-dimethyl-6-{2-oxo-2-[4-(pyridin-3-ylmethyl)-piperazin-1-yl]ethyl}3,4-dihydro-2H-chromen-4-yl)benzenesulfonamide hydrochloride, m.p. 159° C.

$^{13}$C-NMR (101 MHz, MeOH) δ ppm 15.7 (q, 1 C) 19.0 (q, 1 C) 27.0 (q, 1 C) 29.7 (t, 1 C) 39.7 (t, 1C) 40.0 (t, 1 C) 44.2 (t, 1 C) 52.6 (t, 1 C) 53.0 (t, 1 C) 56.0 (d, 1 C) 56.9 (t, 1 C) 74.8 (d, 1 C) 79.9 (s, 1 C) 118.6 (d, 1 C) 124.2 (s, 1 C) 127.8 (s, 1 C) 128.4 (d, 2 C) 128.9 (d, 1 C) 129.3 (d, 3 C) 130.7 (s, 1 C) 130.9 (d, 1 C) 140.6 (s, 1 C) 144.3 (d, 1 C) 145.9 (d, 1 C) 150.6 (s, 1 C) 151.0 (d, 1 C) 153.3 (s, 1 C) 172.3 (s, 1 C).

The compounds of Formula I listed in Table 5 below can also be prepared according to the processes described in the examples above or according to processes analogous thereto:

TABLE 5

Further compounds of Formula I

| Ex. | R¹ | R² | R³ | R⁴ | R⁵ | R⁶ | R⁷ | R⁸ | R⁹ | R¹⁰ | n | *C3 | *C4 |
|---|---|---|---|---|---|---|---|---|---|---|---|---|---|
| 10 | Me | Me | 4-et-phenyl | H | -ethylen-R⁹ | H | H | — | R⁵-ethylen- | bz | 0 | trans | |
| 11 | Me | Me | 4-et-phenyl | H | -ethylen-R⁹ | H | H | — | R⁵-ethylen- | 2-py | 0 | S | R |
| 12 | Me | Me | 4-et-phenyl | H | -ethylen-R⁹ | H | H | — | R⁵-ethylen- | 4-py | 0 | S | R |

Ex. = number of example;
Me = methyl;
4-et-phenyl = 4-ethylphenyl;
-ethylen-R⁹ = formation of ethylen bridge together with substituent R⁹;
R⁵-ethylen- = formation of ethylen bridge together with substituent R⁵;
bz = benzyl;
2-/3-/4-py = 2-/3-/4-pyridinyl;
S, R: absolute stereochemistry at designated carbon atom according to Cahn-Ingold-Prelog nomenclature;

The following spectroscopic data were measured in the $^{13}$C-NMR:

EXAMPLE 10

HCL Salt $^{13}$C-NMR (101 MHz, DMSO-D6) δ ppm 15.1 (q, 1 C) 18.7 (q, 1 C) 26.4 (q, 1 C) 27.9 (t, 1 C) 37.8 (t, 1 C) 38.3 (t, 1 C) 41.9 (t, 1 C) 50.1 (t, 1 C) 50.5 (d, 1 C) 54.1 (d, 1 C) 58.6 (t, 1 C) 72.3 (d, 1 C) 78.5 (s, 1 C) 116.4 (d, 1 C) 122.8 (s, 1 C) 126.7 (d, 2 C) 126.8 (s, 1 C) 127.9 (d, 2 C) 128.7 (d, 2 C) 129.1 (d, 1 C) 129.2-129.6 (2d,s, 3 C) 131.3 (d, 2 C) 140.0 (s, 1 C) 147.9 (s, 1 C) 151.1 (s, 1 C) 169.0 (s, 1 C)

EXAMPLE I

Capsules containing (3S,4R)—N-{6-[2-(4-Benzylpiperazin-1-yl)-2-oxoethyl]-3-hydroxy-2,2-dimethylchroman-4-yl}-4-n-propylbenzenesulfonamide:
Capsules with the following composition per capsule were prepared:

| | |
|---|---|
| (3S,4R)-N-{6-[2-(4-Benzylpiperazin-1-yl)-2-oxoethyl]-3-hydroxy-2,2-dimethylchroman-4-yl}-4-n-propylbenzenesulfonamide | 20 mg |
| Corn starch | 60 mg |
| Lactose | 300 mg |
| EA | q.s. |

The active substance, the corn starch and the lactose were processed into a homogenous pasty mixture using EA. The paste was ground and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 9 mg | and then poured into 400 mg capsules (=capsule size 0).

The foregoing description and following examples have been set forth merely to illustrate the invention and are not intending to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to formula I,

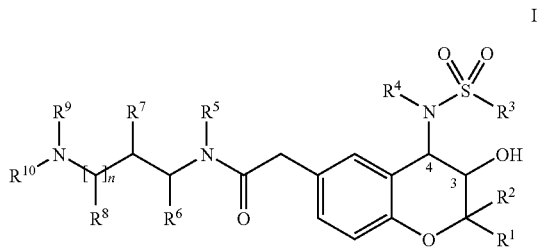

wherein
R¹ is $C_{1-4}$-alkyl;
R² is $C_{1-4}$-alkyl;
R³ is phenyl which is optionally substituted 1 to 3 times by any of halogen, $C_{1-6}$-alkyl or $C_{1-4}$-alkoxy;
R⁴ is hydrogen; $C_{1-6}$-alkyl or $C_{3-7}$-cycloalkyl-$C_{1-4}$-alkyl,
R⁶ is hydrogen; and
R⁷ is hydrogen; and
R⁸ is hydrogen; and
R¹⁰ is $C_{1-6}$-alkyl; phenyl-$C_{0-4}$-alkyl or pyridinyl-$C_{0-4}$-alkyl; provided that R¹⁰ is not phenyl when R⁵ and R⁹ together form $C_2$-alkylene;
R⁵ and R⁹ together form $C_{1-3}$-alkylene; and
n is 0 or 1,
or a physiologically compatible salt thereof.

2. A compound according to claim 1, wherein R¹ and R² are each methyl.

3. A compound according to claim 1, wherein R³ is 4-ethylphenyl.

4. A compound according to claim 1, wherein R⁴ is hydrogen, $C_{1-6}$-alkyl or cyclopropylmethyl.

5. A compound according to claim 1, wherein R¹⁰ is $C_{1-6}$-alkyl; phenyl-$C_{1-4}$-alkyl or pyridinyl-$C_{1-4}$-alkyl.

6. A compound according to claim 1, wherein R¹⁰ is benzyl or pyridinylmethyl.

7. A compound according to claim 1, wherein said compound is selected from the group consisting of
N-{6-[2-(4-benzyl-piperazin-1-yl)-2-oxo-ethyl]-3-hydroxy-2,2-dimethyl-chroman-4-yl}-4-ethyl-benzenesulfonamide;

4-ethyl-N-{3-hydroxy-2,2-dimethyl-6-[2-oxo-2-(4-pyridin-3-ylmethyl-piperazin-1-yl)-ethyl]-chroman-4-yl}-benzenesulfonamide;

4-ethyl-N-{3-hydroxy-2,2-dimethyl-6-[2-oxo-2-(4-pyridin-2-ylmethyl-piperazin-1-yl)-ethyl]-chroman-4-yl}-benzenesulfonamide and 4-ethyl-N-{3-hydroxy-2,2-dimethyl-6-[2-oxo-2-(4-pyridin-4-ylmethyl-piperazin-1-yl)-ethyl]-chroman-4-yl}-benzenesulfonamide.

8. A compound according to claim 1 which is 4-ethyl-N-{3-hydroxy-2,2-dimethyl-6-[2-oxo-2-(4-pyridin-3-ylmethyl-piperazin-1-yl)-ethyl]-chroman-4-yl}-benzenesulfonamide.

9. A pharmaceutical composition, containing a pharmacologically active quantity of a compound of formula I according to claim 1 and at least one auxiliary or carrier.

10. A method of treating cardiovascular disease in a mammal or human, said method comprising administering to said mammal or human a pharmaceutically effective amount of a compound according to claim 1.

11. The method of claim 10, wherein the cardiovascular disease is an arrhythmia.

12. A process for the preparation of a compound corresponding to Formula I,

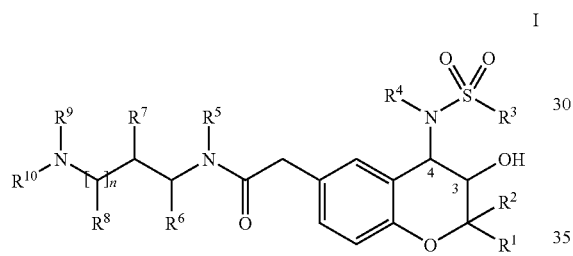

wherein
$R^1$ is $C_{1-4}$-alkyl;
$R^2$ is $C_{1-4}$-alkyl;
$R^3$ is phenyl which is optionally substituted 1 to 3 times by any of halogen, $C_{1-6}$-alkyl or $C_{1-4}$-alkoxy;
$R^4$ is hydrogen; $C_{1-6}$-alkyl or $C_{3-7}$-cycloalkyl-$C_{1-4}$-alkyl,
$R^6$ is hydrogen; and
$R^7$ is hydrogen; and
$R^8$ is hydrogen; and
$R^{10}$ is $C_{1-6}$-alkyl; phenyl-$C_{0-4}$-alkyl or pyridinyl-$C_{0-4}$-alkyl; with the proviso that $R^{10}$ is not phenyl when $R^5$ and $R^9$ together form $C_2$-alkylene;
$R^5$ and $R^9$ together form $C_{1-3}$-alkylene; and
n is 0 or 1,
or a physiologically compatible salt thereof,
said method comprising the steps of reacting
a) a compound corresponding to the general Formula II,

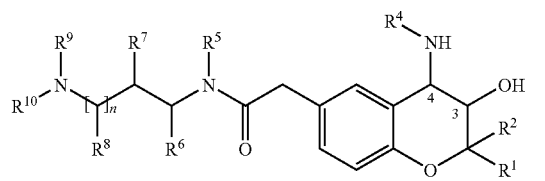

wherein $R^1$, $R^2$, $R^4$, $R^5$, $R^6$, $R^7$, $R^8$, $R^9$, $R^{10}$ and n have the above meanings, with a compound of the general formula III,

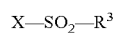

$$X—SO_2—R^3 \quad \quad III$$

wherein $R^3$ has the above meaning, and X is a cleavable leaving group, or
reacting
b) a compound corresponding to general Formula IV

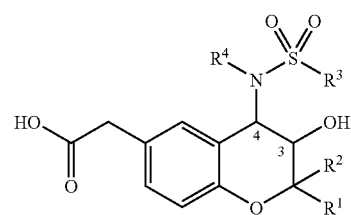

wherein $R^1$, $R^2$, $R^3$ and $R^4$ have the above meanings, with a compound corresponding to general Formula V,

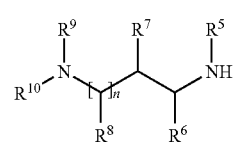

wherein $R^5$, $R^6$, $R^7$, $R^8$, $R^9$, $R^{10}$ and n have the above meanings, and optionally converting resulting free compounds corresponding to Formula I into their physiologically compatible salts, or converting salts of the compounds corresponding to Formula I into free compounds corresponding to Formula I.

13. A compound corresponding to formula II,

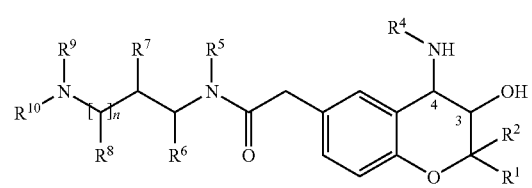

wherein
$R^1$ is $C_{1-4}$-alkyl;
$R^2$ is $C_{1-4}$-alkyl;
$R^4$ is hydrogen; $C_{1-6}$-alkyl or $C_{3-7}$-cycloalkyl-$C_{1-4}$-alkyl,
$R^6$ is hydrogen; and
$R^7$ is hydrogen; and
$R^8$ is hydrogen; and
$R^{10}$ is $C_{1-6}$-alkyl; phenyl-$C_{0-4}$-alkyl or pyridinyl-$C_{0-4}$-alkyl; with the proviso that $R^{10}$ is not phenyl when $R^5$ and $R^9$ together form $C_2$-alkylene; or
$R^5$ and $R^9$ together form $C_{1-3}$-alkylene; and
n is 0 or 1
or a salt or solvate thereof.

* * * * *